US007416878B2

(12) United States Patent
Nikolich et al.

(10) Patent No.: US 7,416,878 B2
(45) Date of Patent: *Aug. 26, 2008

(54) **IMMUNOGENIC COMPOSITIONS INCLUDING ROUGH PHENOTYPE *BRUCELLA* HOST STRAINS AND COMPLEMENTATION DNA FRAGMENTS**

(75) Inventors: Mikeljon Nikolich, Takoma Park, MD (US); David Hoover, Rockville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 457 days.

This patent is subject to a terminal disclaimer.

(21) Appl. No.: 10/733,691

(22) Filed: Dec. 11, 2003

(65) Prior Publication Data

US 2005/0142151 A1    Jun. 30, 2005

Related U.S. Application Data

(60) Provisional application No. 60/503,016, filed on Sep. 15, 2003, provisional application No. 60/433,164, filed on Dec. 12, 2002.

(51) Int. Cl.
*C07H 21/00* (2006.01)
*C12N 1/20* (2006.01)
*C12N 15/00* (2006.01)
(52) U.S. Cl. ............... 435/252.3; 435/320.1; 536/23.1
(58) Field of Classification Search ............... 435/252.3, 435/320.1; 536/23.1
See application file for complete search history.

(56) References Cited

U.S. PATENT DOCUMENTS

| 5,643,771 | A | 7/1997 | Stocker | 435/473 |
| 6,149,920 | A | 11/2000 | Boyle et al. | 424/252.1 |
| 6,444,445 | B2 | 9/2002 | Nikolich et al. | 435/69.3 |
| 2005/0208078 | A1* | 9/2005 | Hoffman et al. | 424/272.1 |
| 2005/0266017 | A1* | 12/2005 | Druilhe et al. | 424/191.1 |

FOREIGN PATENT DOCUMENTS

WO    WO 99 37783 A2 *    7/1999

OTHER PUBLICATIONS

Aleksandrov, "A clinical study of postvaccinal reactions to Aero"m Zhurnal Mikrobiologii, Epidemiologii, I Immunobiologii, vol. 22, pp. 31-37 (1962).
Aleksandrov et al., "Reactogenicity and effectiveness of aerogenic", Voyenno-Meditsinskiy Zhurnal, vol. 12, pp. 51-59 (1958).
Araya et al., "Temporal development of protective cell-mediated and humoral immunity in balb/c mice nfected with *Brucella abortus*", Journal of Immunology, vol. 143, No. 10, pp. 3330-3337 (Nov. 15, 1989).
Abomoelak et al., "Humoral and cellular immune responses in mice immunized with recombinatn *Mycobacterium bovis* bacillus calmette-guerin producing a pertussis toxin-tatanus toxin hybrid protein", Infection and Immunity, Oct. 1999, vol. 67, No. 10, pp. 5100-5105.
Bentejac et al., "Vaccination against human brucellosis", Development in Biological Standardization, 1984, 56:531-535.
Brown et al., "Efficient translation of the RpoS sigma factor in *Salmonella typhimurium* requires host factor I, and RNA-binding protein encoded by the hfq gene", Journal of Bacteriology, Jul. 1996, vol. 178, No. 13, pp. 3763-3770.
de Baques et al., "Vaccination with *Brucella abortus* rough mutant RB51 protects BALB/c mice against virulent strains of *Brucella abortus, Brucella melitensis*, and *Brucella ovis*", Infection and Immunity, Nov. 1994, vol. 62, No. 11, pp. 4990-4996.
Bowden et al., "Outer-membrane protein-and rought lipopolysaccharide-specific monoclonal antibodies protect mice against *Brucella ovis*", J. Med. Microbiol., vol. 43 (1995), pp. 344-347.
"*Brucella melitensis* Rev-1 vaccine as a cause of human brucellosis", The Lancet, vol. 342, Sep. 25, 1993, p. 805.
"Brucellosis: an Overview", Emerging Infectious Diseases, vol. 3, No. 2, Apr.-Jun. 1997, pp. 213-221.
"Report of the subcommittee on Brucellosis research," Brucellosis Research: an evaluation, National Academy of Sciences, Washington, D.C., National Academy Press, 1977, pp. 61-77.
Corner et al., "Persistance of *Brucella abortus* strain 19 infection in adult cattle vaccinated with reduced doses", Research in Veterinary Science, 1981, vol. 31, pp. 342-344.
Chen et al., "Immunization against *Brucella* infections", Journal of comparative pathology, 1973, vol. 83, No. 3, pp. 357-367.

(Continued)

*Primary Examiner*—Mark Navarro
(74) *Attorney, Agent, or Firm*—Elizabeth Arwine

(57) ABSTRACT

Live attenuated vaccines against brucellosis and infection by other diseases are described. It has been discovered that trans complementation of the *Brucella* wboA gene can be used to maintain an expression vector in an attenuated *Brucella* host cell in a vaccinee. Further, heterologous antigens can be expressed using this *Brucella* platform, thus effecting a multivalent vaccine against *Brucella* and the disease corresponding to the heterologous antigen.

32 Claims, 10 Drawing Sheets

OTHER PUBLICATIONS

Corbel et al., "Response of the badger (*Meles melse*) to infection", Research in Veterinary Science, 1983, vol. 34, No. 3, pp. 296-300.

Chen et al., "Immunization against *Brucella* infections: immune response of mice, guinea pigs, and *Cynomolgus philipinensis* to live and killed *Brucella melitensis* Strain Rev. I administered by various methods", The Journal of Infectious Diseases, vol. 122, No. 6, Dec. 1970, pp. 489-500.

Cheville et al., "Immune responses and protection against infection and abortion in cattle experimentally vaccinated with mutant strains of *Brucella abortus*", Am. J. Vet. Res., vol. 54, No. 10, Oct. 1993, pp. 1591-1597.

Jacques et al., "Protection conferred on mice by combinations of monoclonal antibodies directed against outer-membrane proteins or smooth lipopolysaccaride of *Brucella*", J. Med. Microbiol., vol. 37 (1992), pp. 100-103.

Chatfield et al., "Evaluation of *Salmonella typhimurium* strains harbouring defined mutations in htrA and aroA in the murine salmonellosis model", Microbial Pathogenesis, 1992, vol. 12, pp. 135-151.

Crawford et al., "Deletion of purE attenuates *Bruclla melitensis* infection in mice", Infection and Immunity, Jun. 1996, vol. 64, No. 6, pp. 2188-2192.

Comerci et al., "Vector development for the expression of foreign proteins in the vaccine strain *Brucella abortus* S19", Infection and Immunity, Aug. 1998, vol. 66, No. 18, pp. 3862-3866.

Cheville et al., "Bacterial persistence and immunity in goats vaccinated with a purE deletion mutant or the parental 16M Strain of *Brucella melitensis*", Infection and Immunity, Jul. 1996, vol. 64, No. 7, pp. 2431-2439.

Dubray et al., "Isolation of three *Brucella abortus* cell-wall antigens protective in murine expermental brucellosis", Annals of Veterinary Research, 1980, vol. 11, No. 4, pp. 367-373.

de Bagues et al., "An ELISA with *Brucella lipopolysaccharide* antigen for the diagnosis of *B. melitensis* infection in sheep and for the evaluation of serological responses following subcutaneous or conjuctival *B. melitensis* strain Rev-1 vaccination", Veterinary Microbiology, 30 (1992), pp. 233-241.

de Bagues et al., "Responses of ewes to *B. melitensis* Rev-1 vaccine administered by subcutaneous or conjunctival routes at different stages of pregnancy", Annals of Veterinary Research, 1989, vol. 20, pp. 205-213.

Drazek et al., "Deletion of purE attenuates *Brucella melitensis* 16M for growth in human monocyte-derived macrophages", Infection and Immunity, Sep. 1995, vol. 63, No. 9, pp. 3297-3301.

de Bagues et al., "Vaccination with *Brucella abortus* rough mutant RB51 protects BALB/c mice against virulent strains of *Brucella abortus, Brucella melitensis*, and *Brucella ovis*", Infection and Immunity, No. 1994, vol. 62, No. 11, pp. 4990-4996.

Edmonds et al., "Attenuation of a *Brucella abortus* mutant lacking a major 25 kDa outer membrane protein in cattle", AJVR, vol. 62, No. 9, Sep. 2001, pp. 1461-1466.

Elberg et al., "Immunization against *Brucella* infection", Bull. Wld. Hlth. Org., (1962), vol. 26, pp. 421-436.

Elberg, "Caprine Immunization Against Brucellosis", Bull. Wod. Hlth. Org., (1958), vol. 19, pp. 711-724.

Elberg, "A guide to the diagnosis, treatment and prevention of human brucellosis", 1981, pp. 1-71.

Fensterbank et al., "Vaccination of ewes by a single conjunctival administration of *Brucella melitensis* Rev-1 vaccine", Annals of Veterinary Research, (1985) vol. 16, No. 4, pp. 351-356.

Fensterbank et al., "Efficacy of *Brucella melitensis* Rev-1 vaccine against *Brucella ovis* infeciton in rams", Annals of Veterinary Research, (1982), vol. 13, No. 2, pp. 185-190.

Fernandez-Prada et al, "Deletion of wboA enhances activation of the lectin pathway of complement in *Brucella abortus* and *Brucella melitensis*", Infection and Immunity, Jul. 2001, vol. 69, No. 7, pp. 4401-4416.

Fleischner and Meyer, "Preliminary observations on teh pathogenicity for monkeys of the bacillus abortus bovinus", Transactions of the American Pediatric Society, vol. 32, 1920, pp. 141-145.

Gross et al., "Expression and Bactericidal activity of nitric oxide synthase in *Brucella-suis*-infected murine macrophages", Infection and Immunity, Apr. 1998, vol. 66, No. 4, pp. 1309-1316.

Highlander et al., "Expression of the Pasteurella haemolytica leukotoxin is inhibited by the locus that encodes an ATP-binding cassette homolog", Infection and Immunity, Sep. 1993, vol. 61, No. 9, pp. 3942-3951.

Hadjichristodoulou et al., "Tolerance of the human brucellosis vaccine and the intradermal reaction test for brucellosis", Eur. J. Clin. Microbiol. Infect. Dis., Feb. 1994, vol. 13, No. 2, pp. 129-134.

Howe et al, "Acute brucellosis among laboratory workers", New England Journal of Medicine, vol. 236, No. 20, pp. 741-747, May 15, 1947.

Huddleson and Hallman, "The pathogenicity of the species of the genus *Brucella* for monkeys", Baceteriological and Pathological Sections of the Michigan Agricultural Experiment Station, 1929, pp. 293-303.

Hensel et al., "Simultaneous identification of bacterial virulence genes by negative selection", Science, vol. 269, Jul. 21, 1995, pp. 400-403.

Hoover et al., "Protection of mice against brucellosis by vaccination with *Brucella melitensis* WR201 (16MdeltapurEK)", Infection and Immunity, No. 1999, vol. 67, No. 11, pp. 5877-5884.

Jones et al., "Survival of virulent and attenuated strains of *Brucella abortus* in nofrmal and gamma interferon-activated murine peritoneal macrophages", Infection and Immunity, Jul. 1992, vol. 60, No. 7, pp. 3011-3014.

Jacques et al., "Induction of antibody and protective responses in mice by *Brucella* O-polysaccharide-BSA conjugate", Vaccine, No. 9, Dec. 1991, pp. 896-900.

Johnson et al., "The role of a stress-response protein in *Slmonella typhimurium* virulence", Molecular Microbiology (1991), 5(2), pp. 401-407.

Kaneene et al., "Whole-blood lymphocyte stimulation assay for measurement of cell-mediated immune responsees in bovine brucellosis", Journal of Clinical Microbiology, Jun. 1978, vol. 7, No. 6, pp. 550-557.

Kohler et al., "Participation of the molecular chaperone DnaK in intracellular growth of *Brucella suis* within U937-derived phagocytes", Molecular Microbiology, (1996), 20(4), pp. 701-712.

Kruse et al., "Cross infection with eighteen pathogens among caged laboratory animals", Laboratory Animal Care, Jun. 1970, 20(3), pp. 541-560.

Limet et al., "Immunity conferred upon mice by anti-LPS monoclonal antibodies in murine brucellosis", Ann. Inst. Pateur/Immunol., 1987, vol. 138, pp. 417-424.

Lord et al., "Venzuelan field trials of vaccines against brucellosis in swine", AJVR, vol. 59, No. 5, May 1998, pp. 546-551.

Liu, et al., "Glycosyl transferases of O-antigen biosynthesis in *Salmonella enterica*: identification and characterization of transferase genes of groups B, C2, and E1", Journal of Bacteriology, Jun. 1993, vol. 175, No. 11, pp. 3408-3413.

Leal-Klevezas et al., "Molecular detection of *Brucella* spp: rapid identification of *B. abortus* boviar I using PCR", Acrhives of Medical Research, vol. 26, No. 3, pp. 363-267 (1995).

Mense et al., "Bacterilogic and histologic features in mice after intranasal inoculation of *Brucella melitensis*", AJVR, Nol. 62, No. 3, Mar. 2001, pp. 398-405.

Meador et al., "Experimentally induced *Bruclla abortus* infection in pregnant goats", Am.J.Vet.Res., vol. 47, No. 11, Nov. 1986, pp. 2337-2342.

Marmur, "A procedure for the isolation of deoxyribonucleic acid from micro-organisms", J. Mol. Biol. (1961), vol. 3, pp. 208-218.

Mousa et al.,"The nature of human brucellosis in Kuwait: study of 379 cases", Reviews of Infectious Diseases, vol. 10, No. 1, 1988, pp. 211-217.

McFarland et al., "Effect of different purine auxotrophic mutations on mouse-virulence of a Vi-positive strain of *Salmonella dublin* and of two strains of *Salmonella typhimurium*", Microbial Pathogenesis, 1987, vol. 3, pp. 129-141.

Mesnage et al., "Cell surface-exposed tetanus fragment C produced by recombinant *Bacillus anthracis* protects against tetanus toxin", Infection and Immunity, Sep. 1999, vol. 67, No. 9, pp. 4847-4850.

Marshall et al., Use of the stationary phase inducible promoters, spv and dps, to drive heterologous antigen expression in *Salmonella* vaccine strains, Vaccine 18 (2000), pp. 1298-1306.
McQuiston et al., "Creation of rough *Brucella* mutants using allelic replacement of the rfbU gene encoding mannosyl transferase", CRWAD, Nov. 1995, two pages.
McQuiston et al., "Genetic characterization of a Tn5-disrupted glycosyltransferase gene homolog in *Brucella abortus* and its effect on lipopolysaccharide composition and virulence", Infection and Immunity, Aug. 1999, vol. 67, No. 8, pp. 3830-3835.
Mahan et al., "Selection of bacterial virulence genes that are specifically induced in hose tissues", Science, vol. 259, Jan. 29, 1993, pp. 686-688.
Nicoletti, Paul, Chapter 11 "Vaccination", from Animal Brucellosis, Boca Raton: CFC Press, 1990, pp. 283-300.
Nicoletti et al., "Protection by oral administration of *Brucella abortus* strain 19 against an oral challenge exposure iwth a pathogenic strain of *Brucella*", published as journal series article No. 3975, as a contribution of the Flrida Agriculture Experiment Station, Sep. 1983, pp. 1641-1643.
Nicoletti, Paul, Chapter 4 "Relationship Between Animal and Human Disease", from Brucellosis: clinical and laboratory aspects, Boca Raton: CFC Presss, 1989, pp. 97-126.
Plommet et al., "Vaccination against bovine brucellosis with a low dose of strain 19 administered by the conjunctival route", Annals of Veterinary Research, 1975, 6(4) pp. 345-356.
Plommet et al., "Immunity of *Brucella abortus* induced in mice by popliteal lymph node restricted strain 19 vaccination", Annals of Veterinary Research, 1989, 20(1) pp. 73-81.
Plommet et al., "Anti-brucella immunity transferred by immune serum . . . ", Annals of Veterinary Research, 1986, 17(2) pp. 169-175.
Pardon et al., Killed vaccine in adjuvant and protection of mice against an intraperitoneal challenge of *Brucella*: kinetic studies, Annals of Veterinary Research, 1976, 7(4) pp. 297-305.
Pardon et al., "Resistance of nromal or immunized guinea pigs against a subcutaneous challenge of *Brucella abortus*", Annals of Veterinary Research, 1978, 9(3) pp. 419-425.
Pavlov et al., "In vivo and in vitro effects of monoclonal antibody to ly antigens on immunity to infection", Cellular Immunology , 71, pp. 127-138 (1982).
Pardon, "Resistance against a subcutaneous *Brucella* challenge of mice immunized with living or dead *Brucella* or by transfer of immune serum", Ann. Immunol. (Inst. Pasteur), 1977, 128 C, pp. 1025-1037.
Pardon and Marly, "Resistance of *Brucella abortus* infected mice to intravenous or intraperitoneal *Brucella* reinfection", Ann. Immunol. (Inst. Pasteur), 1976, 127 C, pp. 57-70.
Pugh et al., "Immunogenicity of *Brucella*-extracted and recombinant protein vaccines in CD-1 and BALB/c mice", Am. J. Vet. Res., vol. 51, No. 9, Sep. 1990, pp. 1413-1420.
Pickett et al., "In vivo characterization of the murine intranasal model for assessing the immunogenicity of attenuated *Salmonella enterica* serovar typhi strains as live mucosal vaccines and as live vectors", Infection and Immunity, Jan. 2000, vol. 68, No. 1, pp. 205-213.
Pardon et al., "Serological and allergic reactions of ewes after simultaneous vaccinations with two living attenuated strains *Brucella* and *Salmonella*", Ann. Rech. Vet, (1990), 21, pp. 153-160.
Quandt and Hynes, "Versatile suicide vectors which allow directe selection for gene replacement in Gram-negative bacteria", Gene, 127 (1993), pp. 15-21.
Roop et al., "Experimental infection of goat fetuses inutero with a stable, rough mutant of *Brucella abortus*", Research in Veterinary Science, 1991, 51, pp. 123-127.
Roop, et al., "Virulence of *Brucella melitensis* hfq, katE and bacA mutants in pregnant goats", p. 93, Brucellosis 2000, 53rd brucellosis research conference, Sep. 7-9, 2000, Nimes, France.
Rigby and Fraser, "Plasmid transfer and plasmid-mediated genetic exchange in *Brucella abortus*", Can. J. Vet. Res., 1989, 53:326-330.
Sharma et al., "Preparation of electrocompetent *E. coli* using salt-free growth medium", Biotechniques, vol. 20, No. 1, 1996, pp. 42-44.
Schurig et al., "Biological properties of RB51; a stable rough strain *Brucella abortus*", Veterinary Microbiology, 28 (1991), pp. 171-188.
Pardon et al., "Serological and ellergic reactions of ewes after simultaneous vaccinations with two living attenuated strains of *Brucella* and *Salmonella* ", Annals of Veterinary Research, 1990, 21(2), pp. 153-160.
Spink et al., "Immunization with viable *Brucella* organisms", Bull. Wld. Hlth.Org., 1962, vol. 26, pp. 409-419.
Tabatabai et al., "Monophosphoryl lipid A-induced immune enhancement of *Brucella abortus* salt-extractable protein and lipopolysaccharide vaccines in BALB/c mice", Am. J. Vet. Res., vol. 52, No. 10, Oct. 1992, pp. 1900-1907.
Tsui et al., "Characterization of broadly pleiotropic phenotypes caused by an hfq insertion mutation in *Escherichia coli* K-12", Molecular Microbiology (1994), 13(1), pp. 35-49.
Toebe et al., "Evaluation of immunogenicity of an oral *Salmolella* vaccine expressing recombinant *Plasmodium berghei* merozoite surface protein-1", Am. J. Trop.Med. Hyg., 56(2), 1997, pp. 192-199.
Taylor and Rose, "A correction in the nucleotide sequence of the Tn903 kanamycin resistance determinant in pUC4K", Nucleic Acids Research, vol. 16, No. 1, 1988, p. 358.
Vemulapalli et al., "Identification of an IS711 element interrupting the wboA gene of *Brucella abortus* vaccine strain RB51 and a PCR assay to distinguish strain RB51 from other *Brucella* species and strains", Clinical and Diagnostic Laboratory Immunology, Sep. 1999, vol. 6, No. 5, pp. 760-764.
Vemulapalli et al., "*Brucella abortus* RB51: enhancing vaccine efficacy and developming multivalent vaccines", Veterinary Microbiology, 90 (2002), pp. 521-532.
Vemulapalli et al., "*Brucella abortus* strain RB51 as a vector for heterologous protein expression and induction of specific Th 1 type immune responses", Infection and Immunity, Jun. 2000, vol. 68, No. 6, pp. 3290-3296.
Vemulapalli et al., "Cloning and sequencing of yajC and secD homologs of *Brucella abortus* and demonstration of immune responses to yacC in mice vaccinated with *B abortus* RB51", Infection and Immunity, Dec. 1998, vol. 66, No. 12, pp. 5684-5691.
Vemulapalli et al., "Overexpression of protective antigen as a novel approach to enhance vaccine efficacy of *Brucella abortus* Strain RB51", Infection and Immunity, Jun. 2000, vol. 68, No. 6, pp. 3286-3289.
Vemulapalli et al., "Complementation of *Brucella abortus* RB51 with a functional wboA gene results in 0-antigen synthesis and enhanced vaccine efficacy but no change in rough phenotype and attenuation", Infection and Immunity, Jun. 2000, vol. 68, No. 7, pp. 3927-3932.
Vemulapalli et al., "Characterization of specific immune responses of mice inoculated with recombinant vaccinia virus expressing an 18-kilodalton outer membrane protein of *Brucella abortus*", Clinical and Diagnostic Laboratory Immunology, Jan. 2000, vol. 7, No. 1, pp. 114-118.
Vemulapalli et al., "Enhanced efficacy of recombinant *Brucella abortus* RB51 vaccines against *B. melitensis* infection in mice" Veterinary Microbiology 102 (2004), pp. 237-245.
Wahl et al., "Isolation of human mononuclear cell subsets by counterflow centrifugal elutriation (CCE)", Cellular Immunology, 85, pp. 373-383 (1984).
Wu et al., "Construction and immunogenicity in mice of attenuated *Salmonella typhi* expressing *Plasmodium falciparum* merozoite surface protein 1 (MSP-1) fused to tetanus toxin fragment C", Journal of Biotechnology, 83 (2000), pp. 125-135.
Winter et al., "Protection of BALB/c mice against homologous and heterologous species of *Brucella* by rough strain vaccines derived from *Brucella melitensis* and *Brucella suis* biovar 4", AJVR, vol. 57, No. 5, May 1996, pp. 677-683.
Young, E., Chapter 9 "Treatment of Brucellosis in Humans", from Brucellosis: Clinical and Laboratory Aspects . . . , 1989, Boca Raton, Florida, CRC Press, pp. 127-141.
Young, E., Review Articles "Human Brucellosis", Reviews of Infectious Diseases, vol. 5, No. 5, Sep.-Oct. 1983, pp. 821-842.
Zhan et al., "Cytokine response of T-cell subsets from *Brucella abortus*-infected mice to soluble *Brucella* proteins", Infeciton and Immunity, Jul. 1993, vol. 61, No. 7, pp. 2841-2847.
Sulitzeanu, Dov, "Mechanism of Immunity Against *Brucella*", Nature, vol. 181, pp. 495-497 (1958).

Sulitzeanu, Dov, "The fate of killed, radioiodinated *Brucella abortus* injected into mice", J. Immunol., vol. 82, pp. 304-312 (1959).

Sulitzeanu, Dov., "Passive protection experiments with *Brucella antisera*", J. Hyg., vol. 53, pp. 133-142 (1955).

Halpern et al., "Cloning and expression of functional fragment C of tetanus toxin", Infection and Immunity, Apr. 1990, vol. 58, No. 4, pp. 1004-1009.

Cloeckaert A, Grayon M, Verger JM, Letesson JJ, Godfroid F. Conservation of seven genes involved in the biosynthesis of the lipopolysaccharide O side chain in *Brucella* spp. Res Microbiol. Apr. 2000;151(3):209-16.

Godfroid F, Cloeckaert A, Taminiau B, Danese I, Tibor A, de Bolle X Mertens P, Letesson JJ. Genetic organisation of the lipopolysaccharide O-antigen biosynthesis region of *Brucella melitensis* 16M (wbk.) Res Microbiol. Oct. 2000;151(8):655-68.

Allen CA, Adams LG, Ficht TA. Transposon-derived *Brucella abortus* rough mutants are attenuated and exhibit reduced intracellular survival. Infect Immun. Mar. 1998;66(3):1008-16.

Foulongne V, Bourg G, Cazevieille C, Michaux-Charachon S, O'Callaghan D. Identification of *Brucella suis* genes affecting intracellular survival in an in vitro human macrophage infection model by signature-tagged transposon mutagenesis. Infect Immun. Mar. 2000;68(3):1297-303.

Godfroid F, Taminiau B, Danese I, Denoel P, Tibor A, Weynants V, Cloeckaert A, Godfroid J, Letesson JJ. Identification of the perosamine synthetase gene of *Brucella melitensis* 16M and involvement of lipopolysaccharide O side chain in *Brucella* survival in mice and in macrophages. Infect Immun. Nov. 1998;66(11):5485-93.

Godfroid F, Cloeckaert A, Taminiau B, Danese I, Tibor A, de Bolle X, Mertens P, Letesson JJ. Genetic organisation of the lipopolysaccharide O-antigen biosynthesis region of *Brucella melitensis* 16M (wbk). Res Microbiol. Oct. 2000;151(8):655-68.

McQuiston JR, Vemulapalli R, Inzana TJ, Schurig GG, Sriranganathan N, Fritzinger D, Hadfield TL, Warren RA, Lindler LE, Snellings N, Hoover D, Halling SM, Boyle SM. Genetic characterization of a Tn5-disrupted glycosyltransferase gene homolog in *Brucella abortus* and its effect on lipopolysaccharide composition and virulence. Infect Immun. Aug. 1999;67(8):3830-5. Erratum in: Infect Immun Sep. 2000;68(9):5471.

Monreal D, Grillo MJ, Gonzalez D, Marin CM, De Miguel MJ, Lopez-Goni I, Blasco JM, Cloeckaert A, Moriyon I. Characterization of *Brucella abortus* O-polysaccharide and core lipopolysaccharide mutants and demonstration that a complete core is required for rough vaccines to be efficient against *Brucella abortus* and *Brucella ovis* in the mouse model. Infect Immun. Jun. 2003;71(6):3261-71.

Winter AJ, Schurig GG, Boyle SM, Sriranganathan N, Bevins JS, Enright FM, Eizer PH, Kopec JD. Protection of BALB/c mice against homologous and heterologous species of *Brucella* by rough strain vaccines derived from *Brucella melitensis* and *Brucella suis* biovar 4. Am J Vet Res. May 1996;57(5):677-83.

Ugalde JE, Czibener C, Feldman MF, Ugalde RA. Identification and characterization of the *Brucella abortus* phosphoglucomutase gene: role of lipopolysaccharide in virulence and intracellular multiplication. Infect Immun. Oct. 2000;68(10):5716-23.

Ugalde JE, Comerci DJ, Leguizamon MS, Ugalde RA. Evaluation of *Brucella abortus* phosphoglucomutase (pgm) mutant as a new live rough-phenotype vaccine. Infect Immun. Nov. 2003;71(11):6264-9.

\* cited by examiner

SEQUENCE LISTING

```
<160> NUMBER OF SEQ ID NOS: 2

<210> SEQ ID NO 1
<211> LENGTH: 2693
<212> TYPE: DNA
<213> ORGANISM: Brucella melitensis
<220> FEATURE:

<400> SEQUENCE: 1
caccttatgt ttgggacatt ttaattagga acgtttatgc                40
cttcggatgc cgtgggcgtg gcatccgcat gagggatggc                80
tttgcgtttc tgcgctttga agatgttgaa attgggttag               120
ggccgcaata tggtggtgta agcctaccag catatgagtt               160
tcgaaatttt gaggggttat ttcttcgccg caccgaagcc               200
actggattgg atggatatac agaccttgga tacgtcccag               240
```

| | |
|---|---|
| atgctgaaca gcgggggttc atctttgcag acggagcagc | 280 |
| cctccacatc aatagcctgt ttgcagataa taacaagggt | 320 |
| gatggcgtgt tttgccaaaa cgtccaatac gtagatggaa | 360 |
| acgatctcaa ttcatccatc gacggcggaa ctgggttcaa | 400 |
| ttttatcaac gtagatcgca taaacatcaa tacgatccgc | 440 |
| agtggtggcc gccggaatat ggcaccagga aatcttaaca | 480 |
| ctgtttccca aggtatctct ttgaatgcaa attgtcagac | 520 |
| tgtaattata ggcaacgcag ttacccacaa ctggtgaagt | 560 |
| cacggttttt atagccaagc tcaggacatt ttggttaatg | 600 |
| gtctgatatc acgtgataat ggcggaaggg ggtacgttgc | 640 |
| agagggttca gcagggtcat ctctcctaaa tggggccgtt | 680 |
| ttcagagata atgtagcagg gaattatttt acaggaggga | 720 |
| caagcgtaaa ccatctcgcg aacttccaac ttcataactc | 760 |
| tagcaccggg gggaaaactt ttgtggccaa tgtcaccaca | 800 |
| aatgggtctg cataacggtc cttgccattt taactataaa | 840 |
| tgagctattc ccgcgcatta agagtagaca cgggaaatca | 880 |
| gtatggctcc gagacatatt acagttatcc taccagctaa | 920 |
| gtaccgaggc ggaagtcttc gagttacgaa gaatatcgtt | 960 |
| cgaatgcttt tgaagggaag tcagaattat ggtgaacagt | 1000 |
| gtcaagttag attggcagta cgtgccgata cctacgatat | 1040 |
| tggggaggag tttcgtgatc ttatcgataa tggtgtagag | 1080 |
| gttcgggaaa tatcattcaa agaagttcct ccagaagatg | 1120 |
| ttaacaatgc taactatttc caaggtagaa atatcgacct | 1160 |
| acagtcgaga acctattggc taatggagga tggccaaaac | 1200 |
| aactgtgccg atagtgacct ttggctagtt gtatcctact | 1240 |
| ctgtagagta tcctattgcc ccgataaggc cgacactgat | 1280 |
| atttgccacc gatttcattc aaaggtacgt acctgatatt | 1320 |
| atttggccac cacggcccgg tgaggggat gctgaggctc | 1360 |
| ttgcgttctt acgacaatca gacggcgtac tagctacaac | 1400 |
| accacacacg cggctggatg cgatttcata cgctggctta | 1440 |
| cctgcgtcca agtttatct tgctccgatg gagtttgacc | 1480 |
| cgacgttttt ggatcgttac cggtcagtgt ctaaggttaa | 1520 |
| ggaaccctat ttcctttggc caaccaaccc aaatgctcac | 1560 |
| aaaaaccatg caaaagcgtt tcaagcgcta gacctatatt | 1600 |
| acggcaaact aaagggtaag ataaagacaa agatagtcgg | 1640 |
| tgtgagtagt gtgcggatgg acccatccca tcgatggcag | 1680 |
| gccaagtacg aaaataaggc ttatgtgaaa tctgtacggg | 1720 |
| aaattgttgc gggtctcgac aacctgaaaa gcaatgttga | 1760 |
| gttcgctggt gaggttgcgg acaaggagta tgcggagctt | 1800 |

-continued

| | |
|---|---|
| cttgcttcag cttgtttcct ttggcatcca actttggcag | 1840 |
| acaacggaac ttttgctgcg gtcgaagcgg catatatggg | 1880 |
| atgtccaacg ctttcaaacg actacccgca gatgcggtat | 1920 |
| atttctaacc gtttcgaaat tcccatgcag tattttaacg | 1960 |
| caaggtctgt gaaggaaatg gcatcagcgc ttaagcaaat | 2000 |
| ggaggagacg ccaatagatg taggtttatt gccaagtcga | 2040 |
| gaaaccctat ctctgcattc gtgggaagct cacgcttccg | 2080 |
| aatactggga tgtgatcgtg agggcagcgg catgaataag | 2120 |
| ctcggcgtgt ttatcggcta taccccaggc caattagatc | 2160 |
| catatcaggg tatttctcgc ttaattgcat tcgtgatcaa | 2200 |
| gggggccttg aaccagggta gcggtgtaac aattgcttgc | 2240 |
| cccggctggc taaaggacga tgtacgtgtt cttttggaag | 2280 |
| atgctgatat cccacttgaa gcggtcaaaa ttatcgcgac | 2320 |
| gaatggtcag cctccattgg cttcgttatg gaagttgaga | 2360 |
| gataagttcc gtaagagacg gacgagtaaa cgaaaacgtc | 2400 |
| tctggctgga gcgctatggs aaaaatgttg caaattttgt | 2440 |
| tgcagaatgg ctttctttgc gctcgtattg ggggattttt | 2480 |
| ttgggggctg ctgcaattgc tgtagtgact attctacttg | 2520 |
| ccgtaccaat tgctatagcc ttcaccgctc ttatcggtct | 2560 |
| tctatttgct cgtcggctta ttagacgtgt tatcaggtca | 2600 |
| aagcttggtt tgtttttca caaaaatgcc aatcaattca | 2640 |
| acaaattaat gtcatctgat gaaaccatcg accggatgag | 2680 |
| ggaacgggaa ttc | 2693 |

<210> SEQ ID NO 2
<211> LENGTH: 410
<212> TYPE: PRT
<213> ORGANISM: Brucella melitensis

<400> SEQUENCE: 2

Met Ala Pro Arg His Ile Thr Val Ile Leu
5 10

Pro Ala Lys Tyr Arg Gly Gly Ser Leu Arg
15 20

Val Thr Lys Asn Ile Val Arg Met Leu Leu
25 30

Lys Gly Ser Gln Asn Tyr Gly Glu Gln Cys
35 40

Gln Val Arg Leu Ala Val Arg Ala Asp Thr
45 50

Tyr Asp Ile Gly Glu Glu Phe Arg Asp Leu
55 60

Ile Asp Asn Gly Val Glu Val Arg Glu Ile
65 70

Ser Phe Lys Glu Val Pro Pro Glu Asp Val
75 80

Asn Asn Ala Asn Tyr Phe Gln Gly Arg Asn

```
                      85                  90
Ile Asp Leu Gln Ser Arg Thr Tyr Trp Leu
                 95                 100

Met Glu Asp Gly Gln Asn Asn Cys Ala Asp
                105                 110

Ser Asp Leu Trp Leu Val Val Ser Tyr Ser
                115                 120

Val Glu Tyr Pro Ile Ala Pro Ile Arg Pro
                125                 130

Thr Leu Ile Phe Ala Thr Asp Phe Ile Gln
                135                 140

Arg Tyr Val Pro Asp Ile Ile Trp Pro Pro
                145                 150

Arg Pro Gly Glu Gly Asp Ala Glu Ala Leu
                155                 160

Ala Phe Leu Arg Gln Ser Asp Gly Val Leu
                165                 170

Ala Thr Thr Pro His Thr Arg Leu Asp Ala
                175                 180

Ile Ser Tyr Ala Gly Leu Pro Ala Ser Lys
                185                 190

Val Tyr Leu Ala Pro Met Glu Phe Asp Pro
                195                 200

Thr Phe Leu Asp Arg Tyr Arg Ser Val Ser
                205                 210

Lys Val Lys Glu Pro Tyr Phe Leu Trp Pro
                215                 220

Thr Asn Pro Asn Ala His Lys Asn His Ala
                225                 230

Lys Ala Phe Gln Ala Leu Asp Leu Tyr Tyr
                235                 240

Gly Lys Leu Lys Gly Lys Ile Lys Thr Lys
                245                 250

Ile Val Gly Val Ser Ser Val Arg Met Asp
                255                 260

Pro Ser His Arg Trp Gln Ala Lys Tyr Glu
                265                 270

Asn Lys Ala Tyr Val Lys Ser Val Arg Glu
                275                 280

Ile Val Ala Gly Leu Asp Asn Leu Lys Ser
                285                 290

Asn Val Glu Phe Ala Gly Glu Val Ala Asp
                295                 300

Lys Glu Tyr Ala Glu Leu Leu Ala Ser Ala
                305                 310

Cys Phe Leu Trp His Pro Thr Leu Ala Asp
                315                 320

Asn Gly Thr Phe Ala Ala Val Glu Ala Ala
                325                 330

Tyr Met Gly Cys Pro Thr Leu Ser Asn Asp
                335                 340

Tyr Pro Gln Met Arg Tyr Ile Ser Asn Arg
                345                 350
```

```
Phe Glu Ile Pro Met Gln Tyr Phe Asn Ala
                355                 360

Arg Ser Val Lys Glu Met Ala Ser Ala Leu
                365                 370

Lys Gln Met Glu Glu Thr Pro Ile Asp Val
                375                 380

Gly Leu Leu Pro Ser Arg glu Thr Leu Ser
                385                 390

Leu His Ser Trp Glu Ala His Ala Ser Glu
                395                 400

Tyr Trp Asp Val Ile Val Arg Ala Ala Ala
                405                 410
```

IMMUNOGENIC COMPOSITIONS INCLUDING ROUGH PHENOTYPE *BRUCELLA* HOST STRAINS AND COMPLEMENTATION DNA FRAGMENTS

This application claims priority from provisional applications 60/433,164, filed Dec. 12, 2002, and 60/503,016, filed Sep. 15, 2003. The entire contents of both of these provisional applications are incorporated herein by reference.

BACKGROUND OF THE INVENTION

*Brucella* infects a significant number of people and livestock in developing countries and infects wild as well as domestic animals in the United States. In addition, *Brucella* is a potential biowarfare agent, having been experimentally weaponized; strains of *Brucella* have been constructed with resistance to multiple antibiotics used to treat the disease. These strains pose a significant morbidity and mortality threat to exposed personnel. Brucellosis symptoms include recurring fever, chills and anxiety. Even though the disease is rarely fatal, once well established, the disease is difficult to treat since the bacteria reside in the bone marrow.

The Department of Bacterial Diseases at the Walter Reed Army Institute of Research is developing live, attenuated *Brucella* mutants as vaccines to protect military troops against infection with *Brucella*, an incapacitating biowarfare threat agent. *Brucella*, a slow-growing, facultative intracellular bacterial parasite of macrophages, causes systemic febrile illness in humans. Its lipopolysaccharide (LPS) is a potent immunomodulator that is being explored as a potential adjuvant to elicit immunity against HIV proteins.

A live attenuated *Brucella* vaccine was developed by the inventors, as described in U.S. Pat. No. 6,444,445 (issued Sep. 3, 2002), the entire contents of which are incorporated herein by reference. This vaccine utilized a strain of *Brucella* having a non-reverting deletion in the rfbU gene (now generally referred to in the art as the wboA gene). The result was a live *Brucella* vaccine that does not cause seroconversion in a vaccinee exposed thereto.

SUMMARY OF THE INVENTION

The inventors have developed an entirely new approach to *Brucella* vaccines, and for using *Brucella* as a platform to deliver antigens from other disease agents.

In particular, this approach uses trans complementation of the rough mutation in a rough purine auxotroph as a means of vaccination against *Brucella* and also a method for in vivo maintenance of plasmids for delivery of foreign antigens in live *Brucella* vaccines. The term "complementation" as used herein means that a gene missing in the *Brucella* strain is provided in trans, or on a satellite DNA such as a plasmid, such that a functional copy of the gene is available for expression to the *Brucella* strain. The presence of a functioning gene results in reverting a mutant rough phenotype *Brucella* strain back into a smooth phenotype. One preferred example of such a gene is the wboA gene, as described in further detail below. However, a wide array of genes integral to lipopolysaccharide biosynthesis may also be used.

We had earlier observed that a wboA, purEK dual deletion mutant of *Brucella melitensis* strain 16M (known as strain WRRP1) is severely attenuated. The WRRP1 strain persisted in BALB/c mouse spleens at low levels for only a week after intraperitoneal (IP) infection, compared with purE and wboA single mutants, which infected in higher numbers and persisted for about 8 weeks. (See FIG. 1) We also found that these wboA/rough mutants were not effective live vaccines in our intranasal challenge mouse model; this led us to focus on smooth attenuated live vaccine candidates.

Rough phenotype is that of any strain that does not make and present the intact O-side chain component of lipopolysaccharide (LPS) on the bacterial cell surface. This phenotype can encompass mutations that alter O-side chain composition, or remove the O-side chain, or even completely remove the LPS. These strains do not cause seroconversion in vaccinees, thus allowing vaccinees to be distinguished from exposure to other *Brucella*.

It has been proposed that live *Brucella* attenuated vectors would be efficient and potentially safe and effective platforms for the intracellular delivery of antigens from other disease agents into mammalian hosts. Combining an attenuated *Brucella* strain (such as, for example, our strain WRRP1) with trans complementation of its rough mutation, we were able to (1) create a live *Brucella* vaccine and immunogenic compositions that are both sufficiently attenuated and are maintained in vivo and in vitro for sufficient periods of time to elicit immunity before safely and naturally clearing out; and (2) provide an intracellular selection for plasmids expressing heterologous antigens. Regarding the latter, we found that this plasmid expression platform is easy to manipulate, to integrate and combine genes for different antigens. Such a platform is also readily used to make a single vaccine against multiple biothreats that is relatively cheap to make and may be used as a vaccine in itself or as part of a prime-boost strategy.

It will be of importance to be able to vaccinate troops against a multiplicity of biothreat agents simultaneously instead of having to go through multiple vaccination protocols with a variety of different vaccines. It will also be important that such vaccines can be quickly made available (manufactured) according to the arising biothreats.

We have developed a vaccine against *Brucella* (considered a biothreat agent) and a multiplicity of unrelated biothreat agents using a live attenuated *Brucella* strain as the delivery vector for protective antigens of multiple biothreat agents. This vaccine will simultaneously protect against *Brucella* infections and against various unrelated biothreat agents of choice. Additionally, the methodology developed will allow quick redesigning of the vaccine to cover newly arising biothreat agents, and/or incorporate antigen variations to broaden immunity.

One main aspect of our invention entails immunogenic compositions and vaccines that are effective against brucellosis infection. These immunogenic compositions and vaccines comprise a live *Brucella* host cell having a rough phenotype, which host cell is preferably sufficiently attenuated or otherwise inactivated (e.g., via chemical, radiation, or ultraviolet means) that upon exposure to a mammal the host cell will not exhibit full virulence of non-attenuated/non-inactivated *Brucella*. The strain must be attenuated or inactivated enough to be safely used in humans. The host strain may be any rough-phenotype mutant that can be complemented, whether otherwise attenuated or not. However, it is preferred that the *Brucella* host strain be at least singly attenuated, and more preferably doubly attenuated or even a triply attenuated.

The host cell is transformed with a recombinant DNA construct replicable in *Brucella* and comprising a promoter recognizable by *Brucella*, and a complementation DNA fragment (such as, for instance, the wboA gene) which is operably linked to the promoter and which complements a rough-conferring mutation in the host cell, thereby effecting a smooth phenotype in the host cell. Thus, the invention combines the advantages of a rough phenotype mutant (attenuation) with a smooth phenotype (enhanced survival in vivo and in vitro, so that an adequate immunogenic reaction is attained). In other words, we have used rough complementation for maintenance of the plasmid in vivo or in vitro, but the resulting *Brucella* strain is still sufficiently attenuated for virulence.

The host bacterium may be transformed (e.g., by electroporation) with a plasmid that can replicate in *Brucella*. Plasmids could also be introduced by mating with another bacterium. Alternatively, a recombinant DNA molecule other than a replicating plasmid may be introduced, for instance, a linear recombinant molecule or a nonreplicating plasmid, that would then integrate into the *Brucella* genome, either by host-mediated homologous recombination or via a recombinant DNA construct.

In another preferred embodiment, the wboA complementation DNA fragment is utilized, which encodes a peptide essential for lipopolysaccharide O-sidechain (OPS) biosynthesis. Since wboA complementation allows expression of LPS, vaccinees will make anti-O side chain antibody, which is believed necessary for protection. When the vaccine is administered to a vaccinee, the lipopolysaccharide O-sidechain polysaccharide is produced in vivo and an antibody to the lipopolysaccharide O-sidechain polysaccharide is produced by the vaccinee in response.

Nearly all *Brucella* rough mutants are known to be attenuated for virulence. The only rough mutant proven to be an effective vaccine is cattle vaccine strain RB51, and this strain is now believed to make low levels of intact LPS.

Another embodiment entails immunogenic compositions and vaccines against infection by brucellosis and/or a non-brucellosis disease, comprising a live attenuated *Brucella* host cell having a rough phenotype. The host cell is sufficiently attenuated that upon exposure to a mammal the host cell will not exhibit full virulence of non-attenuated *Brucella*. The host cell is transformed with a recombinant DNA construct that is able to replicate in *Brucella*. The construct comprises a DNA fragment operably linked to a first promoter recognizable by *Brucella* and encoding a heterologous antigen; and a complementation DNA fragment which is operably linked to a second promoter recognizable by *Brucella*, and which complements a rough-conferring mutation (such as a wboA mutation) in the host cell, thereby effecting a smooth phenotype in the host cell.

The heterologous antigen may be any foreign gene encoding an antigen against which it is desirable to elicit and immune response, in a form that can be produced by genes encoded on a plasmid and expressed in a *Brucella* host. It can either constitute the expressed peptides themselves, or potentially even products of enzymes encoded on the plasmid (polysaccharides, lipids, etc.), as long as it can be made in the *Brucella* host.

Preferably, the heterologous antigen is selected from the group consisting of: Anthrax antigens such as *Bacillus anthracis* protective antigen (PA), inactive variants of Edema Factor and Lethal Factor; plague antigens such as *Yersinia pestis* F1 and V antigens and F1-V fusion proteins; malaria proteins such as circumsporozoite and merozoite antigens, and including antigens of *Plasmodium berghei* (sporozoite and merozoite antigens), *Plasmodium falsiparum, Plasmodium vivax* and *Plasmodium malariae*, including CSP and MSP1 antigens of all of these; *Francisella* antigens, particularly from *Francisella tularensis*; staphylococcal and streptococcal enterotoxin fragment antigens; *Burkholderia* antigens; *Coxiella* antigens; *Clostridium* epsilon toxoids; botulinum toxoids; smallpox antigens; mycobacterial antigens; cancer antigens; HIV antigens; tetanus toxoids (including TetC); diphtheria toxoids; pertussis toxoid; *Helicobacter* antigens; *Borrelia* antigens; *Legionella* antigens; *Bartonella* antigens; vaccinia antigens; antigen-GFP fusions; tagged antigens (6his, V5, etc.), fusions of antigens to secretory signals, fusions of antigens to each other; genes encoding therapeutic molecules or enzymes producing therapeutic molecules; antigens from other parasites, antigens from viruses, and the like. Also contemplated are heterologous genes encoding enzymes that would not serve directly as antigens but would instead synthesize non-protein products in the *Brucella* platform that would themselves function as heterologous antigens—for instance, lipids and polysaccharides. In addition, homologous antigens can be included to enhance immunogenicity.

For the complementation DNA fragment, preferably at least part of the wboA gene is included. More preferably, it encodes a peptide including a lipopolysaccharide O-sidechain, so that when the vaccine is administered to a vaccinee, the lipopolysaccharide O-sidechain peptide is produced in vivo and an antibody to the lipopolysaccharide O-sidechain peptide is produced by the vaccinee in response.

For in all of these embodiments of the invention, the *Brucella* host strain may be any *Brucella* strain with a rough-phenotype mutation that can be complemented on a trans plasmid or the like. It is preferred, however, that the *Brucella* host cell comprises a *Brucella* DNA fragment containing a stable non-reverting deletion mutation, having the nucleotide sequence of SEQ ID NO: 1 modified to delete nucleotides from position 1067 to position 1671. Preferably the *Brucella* host cell is *Brucella melitensis*. More preferably, the *Brucella* host cell is strain WRRP1, having ATCC accession number PTA-3753. The *Brucella* host cell may also be strain WRR51, having ATCC accession number PTA-3754. Both the WRRP1 strain and the WRR51 strain were deposited on Oct. 3, 2001 with the American Type Culture Collection, located at 10801 University Boulevard, Mannassas, Va. 20110-2209.

It is noted that SEQ ID NOs: 1 and 2 (the wboA DNA and amino acid sequences) are derived from *Brucella melitensis*. It is possible to use the wboA gene from any *Brucella* strain (e.g., *Brucella abortus*), as they are functionally interchangeable for the purposes of this invention. It is possible to use any *Brucella* wboA sequence to either complement or replace any other wboA locus. We know that these are interchangeable for allelic replacement, as shown by Winter et al.

WRR51 and WRRP1 are two genetically defined rough mutants of *Brucella melitensis*, and are themselves useful as strains for a live vaccine against brucellosis. These strains differ from *Brucella* live vaccines currently used in livestock because they have genetically defined mutations that were created by deleting DNA from the *Brucella* chromosome. Both strains have a lipopolysaccharide (LPS) defect and thus do not cause the seroconversion that complicates disease screening. Smooth strains currently approved for use in animals are not good candidates for human vaccines because although attenuated, they can still cause disease in humans. WRRP1, is a double deletion mutant that is highly attenuated and is even more unlikely to cause disease in humans. It is preferred that if WRR51 is used, it is combined with another attenuating mechanism, for instance a different secondary mutation or treatment that renders the strain unable to replicate. We also contemplate derivative of WRR51 and WRRP1, with added mutations and/or antibiotic resistance markers removed.

Preferably the promoter is a *Brucella* promoter, although any promoter can be used as long as it is recognizable by *Brucella*.

In another embodiment, our invention entails a recombinant DNA construct replicable in *Brucella*. The DNA construct comprises:
(i) a promoter recognizable by *Brucella*, and
(ii) a complementation DNA fragment which is operably linked to the promoter and which complements a rough-conferring wboA mutation in the host cell, thereby effecting a smooth phenotype in a host cell transformed therewith.

In a further embodiment, the invention includes a recombinant DNA construct replicable in *Brucella*. The DNA construct comprises:
(i) a DNA fragment operably linked to a first promoter recognizable by *Brucella* and encoding a heterologous or homologous antigen, such as is described above and in further detail below, and
(ii) a complementation DNA fragment which is operably linked to a second promoter recognizable by *Brucella* and which complements a rough-conferring mutation in the host cell, thereby effecting a smooth phenotype in a host cell transformed therewith.

Also contemplated by our invention are host cells transformed with any of these DNA constructs.

Our invention encompasses methods for inducing protective immunity to brucellosis in a mammal, comprising the step of administering to a mammal a vaccine comprising a live *Brucella* host cell having a rough phenotype, which host cell is sufficiently attenuated that upon exposure to a mammal the host cell will not exhibit full virulence of non-attenuated *Brucella*. The host cell is transformed with a recombinant DNA construct replicable in *Brucella*, and comprising a promoter recognizable by *Brucella*, and a complementation DNA fragment which is operably linked to the promoter and which complements a rough-conferring mutation in the host cell, thereby effecting a smooth phenotype in the host cell.

Similarly, our invention covers methods for inducing protective immunity to brucellosis or a non-brucellosis disease, or both, in a mammal comprising the step of administering to a mammal a vaccine comprising a live *Brucella* host cell having a rough phenotype, which host cell is sufficiently attenuated that upon exposure to a mammal the host cell will not exhibit full virulence of non-attenuated *Brucella*. The host cell is transformed with a recombinant DNA construct replicable in *Brucella* and comprising a promoter recognizable by *Brucella*; a DNA fragment operably linked to the promoter and encoding a heterologous (or homologous) antigen; and a complementation DNA fragment which is operably linked to the promoter and which complements a rough-conferring mutation in the host cell, thereby effecting a smooth phenotype in the host cell.

In a related embodiment, it is preferred that following administration of the vaccine to the vaccinee, the DNA construct is gradually separated from the *Brucella* host cell, whereupon the *Brucella* host cell reverts to a rough phenotype that is rapidly cleared from the vaccinee. For instance, the DNA construct is gradually separated (e.g., became undetectable) from the *Brucella* host cell in vivo between 28 days and 56 days following administration of the vaccine. In vitro, it was completely lost between 10 and 45 days. This is due to the unstable nature of plasmids in *Brucella*, as described above. A preferred DNA construct is pGSG5 or a derivative thereof.

Figure 9:
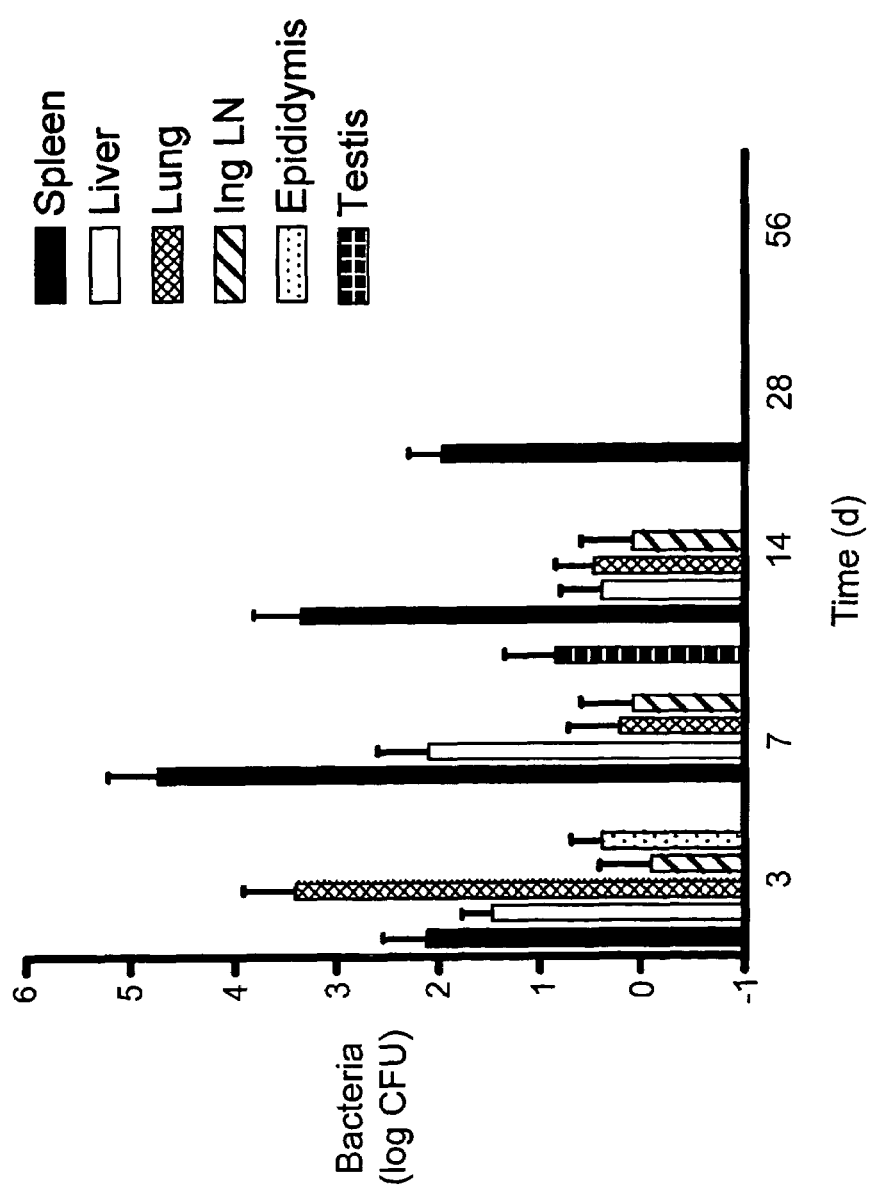

As FIG. 9 shows, looking at the dissemination of the complemented strain to the organs in these mice, numbers recovered from spleens exceeded the other organs, with the exception of the lungs at 3 days. Lungs and livers were also clear by eight weeks. There was low-level dissemination to inguinal lymph nodes up to two weeks. And here was a low level and transient dissemination to the male reproductive organs, gone after 1 week. Early clearance from the male reproductive organs is an aspect that distinguishes WRRP1 bearing pGSG5 from the purine auxotroph WR201, whose persistence in these organs was extended in both mice and nonhuman primates. This increased attenuation is perhaps due to decay of smoothness by loss of the complementing plasmid in the host. This attenuation indicates that severely attenuated WRRP1 with its rough defect trans complemented in this way may be a safe alternative to WR201 that may be as effective in immunizing against *Brucella*. WR201 was our most effective vaccine to date, providing sterile immunity in nonhuman primates.

Figure 10:
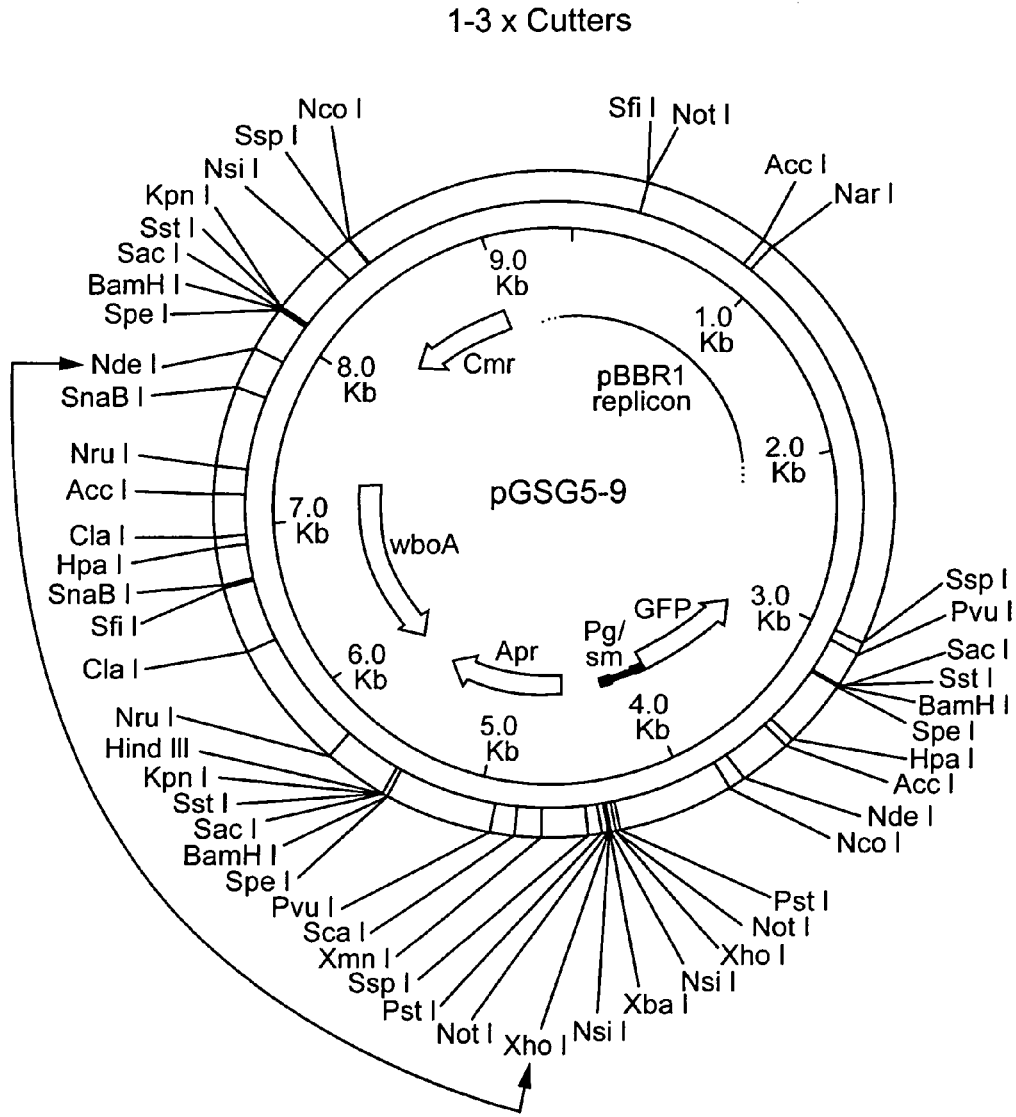

FIG. 10 shows plasmid pGSG5. We note that "1-3X cutters" simply describes the subset of restriction enzyme recognition sites in this particular graphic map. "pGSG5-9" designates the names of sister clones confirmed in the creation of the construct.

DETAILED DESCRIPTION OF THE PREFERRED EMBODIMENTS

This invention was designed in part to solve the problem of the natural loss of plasmids expressing heterologous antigens from live attenuated *Brucella* vaccine platforms when inside the vaccinee. Plasmid loss during bacterial stress is a natural process presumed to enhance the fitness of the bacterium and thus its survival. Since Brucellae reside inside host cells during infection (and vaccination) and thus would be protected against extracellular antibiotic exposure, it is unlikely that giving vaccinees specific antibiotics will do anything to select for plasmids carried in live *Brucella* vaccines. The provision of rough complementation on the antigen expression plasmid in our rough purine auxotrophic dual mutant allows the live vaccine to survive longer in the vaccinee, and also provides a strong selection for maintenance of the plasmid (and thus expression of the heterologous antigen genes it carries) during the course of its survival.

Thus, our invention can be used to vaccinate against both *Brucella* and against any non-*Brucella* antigen(s) encoded by gene(s) that can be expressed from a plasmid in a *Brucella* strain. This includes both protein antigens and also non-protein antigens that could be produced by plasmid encoded genes within the *Brucella* carrier, such as polysaccharides and lipids. This would not be limited to the expression of antigens from pathogenic organisms, but also could include any other antigens to which an immune response would be desired, to include host antigens such as tumor antigens. Any other genes one would want to express within macrophages inside a vertebrate host could be introduced using this platform. This could include genes encoding therapeutic products.

Because of its intracellular location, slow growth in macrophages, and colonization of liver and spleen, *Brucella* is an attractive platform to express heterologous antigens for immunization against a variety of infections. Our invention is based on our discovery that a live attenuated *Brucella* platform can be utilized for intracellular vaccination by delivering antigens from heterologous disease agents into macrophages (host antigen presenting cells). Plasmid (trans) complementation of a crippling mutation such as wboA in a *Brucella* host cell permits longer intracellular persistence, yet retain an attenuated state (such as, for instance, mutation of the purE gene). Intracellular pressure for plasmid maintenance (absent drug selection) thus enhances the utility of the plamsid for foreign antigen expression in mammalian cells. Plasmid-based expression in the *Brucella* platform allows rapid manipulation and combination of antigens from different pathogens in the same vaccine. Such a platform could function as a multivalent vaccine against multiple biothreat agents in a single formulation, and is relatively inexpensive to produce and easily administered. It can be used as a primary vaccine, or as part of a prime-boost strategy.

Live attenuated bacterial and viral vaccine delivery platforms offer the possibility of not only protecting vaccinees against the carrier organism—*Brucella* in this case—but also against antigens from other disease agents expressed in the platform. To that end, another embodiment of the invention entails a multivalent vaccine system in which heterologous antigens are expressed on a rough-complementing plasmid in an attenuated rough (absent normal surface presentation of the O-polysaccharide component of cell envelope lipopolysaccharide) *Brucella* strain containing in its genome, in addition to the mutation or mutations causing the rough phenotype, one or more mutations that independently attenuate the strain for virulence. A preferred embodiment employs mutant *Brucella* strain WRRP1, a dual mutant of *B. melitensis* 16M with deletions in wboA (formerly designated rfbU) and purE genomic loci, which strain is described in U.S. Pat. No. 6,444,445. Also, derivatives of WRRP1 with antibiotic resistance genes removed and/or additional attenuation mutations added would be ideal hosts. But other rough strains of *Brucella* with additional attenuating mutations could also be used to exploit this rough complementation plasmid maintenance approach.

In our preferred embodiment we used complementation of the wboA deletion in WRRP1 by provision of an intact expressed copy of wboA in trans on a plasmid, but other rough complementing gene(s) and rough mutation pairings could be used for this purpose; complementation of multiple rough mutations in the host strain could also be employed. The plasmid used in our preferred embodiment was pGSG5 (FIG. 10), a pBBR1-based plasmid, but any other plasmids that replicate in *Brucella* could also be used for this technology. Our model heterologous antigen here was Green Fluorescent Protein (GFP), because of its relatively easy detection in intracellular bacteria, but obviously it would be more valuable to express other heterologous antigens in *Brucella* for the purposes of constructing new multivalent vaccines. Examples of other heterologous antigens include tetanus toxoid, malarial antigens (such as proteins CSP and MSP, and others), *Bacillus anthracis* protective antigen, *Yersinia pestis*, antigens from other parasites, proteins from other intracellular bacterial pathogens such as *Francisella tularensis, Mycobacteria, Legionella*, and *Coxiella*, antigens from viruses, particularly intracellular invaders such as HIV, other toxoids such as botulinum toxoid, *Epsilon* toxin, tumor antigens, etc. As noted above, we also contemplate heterologous genes encoding enzymes that would not serve directly as antigens but would instead synthesize non-protein products in the *Brucella* platform that would themselves function as heterologous antigens—for instance, lipids and polysaccharides. In addition, homologous antigens can be included to enhance immunogenicity.

One advantage of such multivalent vaccines is that protection against multiple disease agents can be attained with a single vaccine formulation. Another advantage of our rough-complementing plasmid platform is that plasmids are readily manipulated genetically, so gene modules containing a wide variety of foreign antigens can be readily introduced into the complementing plasmid and then into the vaccine strain. This allows for rapid combination of different antigens within a vaccine strain, and also for antigen-expressing plasmids to be moved into better live attenuated vaccine hosts as these are developed.

A distinct advantage of the rough-complementation property of our technology over any other plasmid expression technology used for expression of foreign antigens in live *Brucella* vaccine strains is that it provides an in vivo selective pressure for maintaining the antigen expression from the plasmid after the live vaccine has been introduced into the vaccinee. A further advantage of our delivery platform over many non-*Brucella* platforms is that this bacterium survives in immune cells (macrophages) and is circulated to the spleen and lymphatic system during infection. An attenuated live vaccine can be circulated in the system of the vaccinee and express the antigens it carries until it is eliminated by the immune response (this will vary depending on the degree of attenuation of the carrier strain).

The specific balance of immunity generated by live *Brucella* platforms also appears to be unique. The protective immune response to *Brucella* in our vaccine development work has clearly been shown to involve both a humoral (antibody) response and the cell-mediated component of immunity, thus a diverse immune response to any expressed antigen is also possible. *Brucella* has also been long known as a stimulator of nonspecific immunity early in introduction to the immune system and thus attenuated live *Brucella* vaccines may serve as agents of nonspecific protection and of adjuvancy for any heterologous antigens they express.

A further advantage is that wboA complementation allows expression of LPS, vaccinees will make anti-O side chain antibody, which is believed to be necessary for protection. There is also an additional safety feature in this approach: over time the plasmid appears to be lost, both in vitro and in vivo. We believe this accounts for the reduced persistence and systemic dissemination of WRRP1/pGSG5 versus WR201, since theoretically they are genetically equivalent—both having a deletion in purEK and an intact wboA gene. What is left after plasmid loss is rough WRRP1, which is severely attenuated and rapidly cleared from mice). The vaccine acts like WR201 antigenically early, but then gradually loses plasmid and turns rough (possibly stimulating an anti-rough response as well) and is cleared by the vaccinee earlier (which is desired from a safety standpoint).

It is possible to use live bacterial vectors for immunization against malaria. Expression of CSP and MSP-1 in *Salmonella* and immunization of mice with these constructs protected against *P. berghei*, and induced immune responses against *P. falciparum* MSP-1. Interestingly, development of anti-*P. falciparum* MSP-1 immune responses does not require secretion of antigen from the bacterium or surface display. These data suggest that use of *Brucella* as a platform to deliver malaria antigens in vivo has a high likelihood of success for protection against malaria.

*Brucella*, even attenuated strains, penetrate to the liver. Defense against malaria may involve destruction of liver stage parasites to prevent infection or attack on merozoites to reduce disease. Presence of antibody and Th-type 1 cellular responses, characterized by CD4 and CD8 T-lymphocytes directed at circumsporozoite protein (CSP), are associated with prevention of patent infection after challenge with *P. berghei*, an agent of murine malaria, and *P. falciparum*, which causes a severe form of human malaria. Immune response to merozoite surface protein-1 (MSP-1) of these parasites is associated with reduction in patent infection intensity. Since *P. falciparum* does not cause malaria in mice, the murine *P. berghei* model is used to demonstrate initial proof of concept for malaria vaccine approaches. Vaccines that work in the *P. berghei* model can be reconstructed with *P. falciparum* antigens. Safety and immunogenicity testing in mice and efficacy testing against blood stage infection in nonhuman primates can then lead to human trials. Department of Immunology efforts are directed toward enhancing the potency of immune response against CSP, MSP-1 and other malarial antigens. Genes for these antigens were cloned into expression vectors for use as DNA vaccines and for production of recombinant proteins for clinical vaccine tests and in vitro studies. Movement of these genes into pBBR1MCS should be readily accomplished.

The *Brucella* host strain used in the compositions, vaccines, constructs and methods of this invention may be any rough mutant that can be complemented, whether otherwise attenuated or not. For instance, fully virulent bacterial pathogens (which one would expect a simple complemented rough mutant to be) may be inactivated using known techniques that allow them to continue to be metabolically active in an inviable state and to express proteins such as recombinant heterologous antigens. However, it is preferred that the *Brucella* host strain be singly attenuated (that is, have a single mutation), and more preferred that it be doubly attenuated or even a triply attenuated.

The host bacterium may be transformed (e.g., by electroporation) with a plasmid that can replicate in *Brucella*. However, plasmids could also be introduced by mating with another bacterium. Alternatively, a recombinant DNA molecule other than a replicating plasmid may be introduced, for instance, a linear recombinant molecule or a nonreplicating plasmid, which would then integrate into the *Brucella* genome, either by host-mediated homologous recombination or via a recombinant DNA construct.

Our plasmid pGSG5 is a preferred construct. However, another preferred construct is a derivative of pGSG5 where there is a restriction site inserted between the groES promoter and the GFP gene to allow insertion of genes encoding heterologous antigens. We have two versions: ApaI and SmaI. We have also made a further derivative construct of this first derivative, where the chloramphenicol resistance marker has been deleted. Further, we have made a derivative of pGSG5 where the groES promoter has been replaced with the aphA promoter and a SmaI restriction site inserted between that promoter and the GFP gene to allow insertion of genes encoding other heterologous antigens. We have also made a construct to express MSP1 from *Plasmodium berghei* thatis based on pGSG5 (MSP1 replacing GFP in the construct). In addition, we also have a construct like the latter one, but containing the *Plasmodium berghei* CSP gene minus part of its carboxy terminal-encoding DNA.

In determining the feasibility of a live, attenuated brucellosis vaccine in humans, we developed a live, attenuated vaccine (DpurEK *B. melitensis* strain WR201) that looks extremely promising for development of a multi-valent vaccine. Starting with smooth, virulent *B. melitensis* 16M, we deleted 248 bp of a region consisting of 193 bp of the 3' end of purE, a 37 bp intergenic region and 18 bp of the 5' end of purK. This mutant strain WR201 has several valuable characteristics: 1) it requires supplementation with purines for growth on minimal media; (2) it is attenuated for growth in human and murine macrophages; (3) it establishes transient (4-8 week) infections of liver and spleen in mice; (4) it protects mice against dissemination of bacteria to liver and spleen following intranasal challenge with virulent *B. melitensis*; (5) it establishes similar transient infection in Rhesus macaques after oral administration; and (6) it protects Rhesus macaques from aerosol challenge with $10^7$ virulent *B. melitensis*. This strain is auxotrophic. When administered orally to animals (e.g., mice), it induces protective immunity to subsequent respiratory challenge with 16M. This vaccine, or a derivative with additional deletions, is one preferred Brucella host strain use in this invention.

We have also made a rough mutant (WRR51) from 16M by gene replacement of wboA, which encodes a glycosyl transferase required for production of LPS O-polysaccharide. This mutant is as attenuated as WR201 in mice, but does not protect against intranasal Brucella challenge. Complementation of WRR51 with wboA on low copy number plasmid pBBR1MCS restores the smooth phenotype and correspondingly enhances survival in human macrophages in vitro. (PBR1MCS is a published plasmid based on pBBR1 useful as a shuttle vector from E. coli to Brucella, and it replicates in both.)

Vaccine strain B. melitensis WRRP1 is a preferred strain for both a Brucella vaccine and for heterologous antigen delivery because it carries two different mutations, in purEK and in wboA, that attenuate it. Strain WRRP1 is described in detail in U.S. Pat. No. 6,444,445. To produce WRRP1, we deleted the purEK locus in strain WRR51 (a wboA mutant described in the above patent). This strain is both purine auxotrophic, like WR201, and has a rough phenotype because it lacks O-polysaccharide (OPS) as a component of its outer membrane lipopolysaccharide. Rough strains of Brucellae are consistently less virulent than smooth strains. As expected, WRRP1 is much more attenuated in macrophages and mice than WR201 or a single wboA mutant (WRR51). It survives in mice only about one week after it is injected intraperitoneally. Complementation of this strain with low copy number plasmid that expresses wboA restores a smooth phenotype and reactivity to anti-OPS antibodies, and correspondingly, enhances survival in human macrophages in vitro similar to the parent, virulent strain 16M. Complementation of the extremely attenuated strain WRRP1 with wboA restored its smooth phenotype, and restored virulence in vivo and in vitro similar to that of attenuated WR201. Thus, the wboA-complemented WRRP1 strain has the same protective abilities of vaccine strain WR201.

The advantage of using WRRP1 complemented with wboA instead of WR201 directly is that it would have 2 chromosomal deletions instead of one, further limiting the possibility of reversion of the vaccine to full virulence. The plasmid utilized for complementation can be simultaneously used to express protective antigens (heterologous antigens) of unrelated biothreat.

Expression of heterologous antigens by the Brucella vaccine using plasmid pBBR1MCS and carrying the complementing wboA gene permits immunization with antigens known to protect against other biowarfare threat agents. Use of this plasmid strategy would allow rapid development of a vaccine stably expressing the heterologous antigen, since there would be in vivo selection pressure to retain the plasmid.

Derivatives of WRR51 and WRRP1 are also contemplated, which may have added mutations and/or antibiotic resistance markers removed. Basically, any Brucella strain can serve as the host strain in this invention, as long as it has a rough mutation that can be complemented in the manner described herein. It is preferable that the host strain be attenuated, but as noted above, it is possible to inactivate fully virulent bacterias in such a way as to permit them to express proteins such as recombinant heterologous antigens.

Care would be taken to insure that antigens being expressed in Brucella are not functional virulence factors. For this reason, our research has included use of genes encoding known protective antigens not representing virulence factors or use mutated genes that do not encode complete toxin or virulence factors. There may be some questions about the use of a live Brucella strain, although attenuated, as a human vaccine. We note that it is possible to inactivate a fully virulent bacterial pathogen, such as Brucella, in ways that allows them to continue to be metabolically active in an inviable state and to express proteins such as recombinant heterologous antigens. Pilot experiments indicate that the use of killed Brucella vaccines are not very effective in inducing protective immunity against brucellosis. Therefore, a killed vaccine does not appear to be a good alternative to the live, attenuated vaccine proposed.

Other embodiments of our invention contemplate optimization with different Brucella promoters, and facile integration of new open reading frames (such as, for instance, Invitrogen's Gateway) which would simplify integration of new antigen genes. Possible Brucella promoters include purEK, Kanamycin resistance promoters, groEs promoter, and the virB promoter (the latter especially for in vivo induction). The Brucella platform strain might also be improved by removal of drug resistance markers. Further, additional attenuation of the Brucella strain may be advantageous. We also contemplate incorporating antigen export from the platform, and manipulating the codons of antigens for improved expression in Brucella.

As noted above, variety of heterologous antigens can be effectively expressed in this system. The basic criteria for heterologous antigen expression in our invention is that it is a non-Brucella gene but is able to be expressed directly or indirectly from a plasmid or other recombinant molecule in a Brucella cell, using a promoter recognizable by Brucella. Besides the specific heterologous antigens mentioned above, we also contemplate tetanus toxoid (tetC), Yersinia pestis F1+V and F1–V fusion, multivalent multiagent biodefense antigens, antigens from non-biothreat infectious agents, plague antigens, and combinations of any of these.

As a prototype, we constructed a live, attenuated B. melitensis vaccine strain that expresses protective antigens from three known threat agents and tested it for safety, immunogenicity and protective efficacy in appropriate animal models. For instance, genes encoding some or all of the following can be used: a) protective antigen (PA) from Bacillus anthracis, b) protective C fragment of tetanus toxin and c) protective fragments of V antigen from Yersinia pestis. These antigens may be encoded by a plasmid that also encodes a Brucella gene (wboA), which, as noted above, is preferred for assisting survival of the vaccine strain in vivo and to some extent, protective immunity.

This vaccine could be used in deployable troops in a 1 or 2-dose oral regimen to protect against known, high-likelihood agents including Brucella melitensis and Brucella suis Moreover, use of the plasmid strategy will allow rapid development of vaccines against newly recognized threats as soon as target antigens for vaccination have been identified. Genes encoding these newly identified vaccine antigens could be rapidly inserted in the plasmid and a vaccine strain expressing the antigen made quickly available for testing. This strategy would also allow rapid scale-up to production of quantities sufficient for troop immunization. Since the basic platform of heterologous vaccine delivery could be tested before an emergency occurred, limited safety and efficacy data should be required to allow use of the vaccine expressing novel antigens in the event of a threat requiring rapid response.

Malarial antigens are also contemplated. A Mycobacterium bovis antigen expressed on broad host range plasmid pBBR1MCS in Brucella abortus strain RB51 produced serum antibody in mice and antigen-stimulated IFN-gamma by splenocytes [Vemulapalli, Infect Immun. 68:3290-6, 2000]. Based on our own data, expressing *Plasmodium* antigens from plasmids in our candidate strains will likely induce strong immune responses. Defense against malaria may involve destruction of liver stage parasites to prevent infection or attack on merozoites to reduce disease. Presence of antibody and Th-type 1 cellular responses directed at circumsporozoite protein (CSP) are associated with prevention of patient infection after challenge with *P. berghei*, an agent of murine malaria, and *P. falciparum*, which causes a severe form of human malaria. The murine *P. berghei* model is used to demonstrate initial proof of concept for malaria vaccine approaches. Immune response to merozoite surface protein-1 (MSP-1) of *Plasmodium* parasites is associated with reduction in patent infection intensity. With this invention, our efforts are directed toward enhancing the potency of immune response against CSP, MSP-1 and other malarial antigens. Recombinant genes for these antigens were cloned in expression plasmids for use as DNA vaccines and for recombinant protein production in bacteria. Expression of these recombinant genes into *Brucella* has been accomplished using appropriate *Brucella* promoters. For instance, purER promoter gives low-level constitutive expression, while Kan promoter gave high constitutive expression, and groES promoter gave intermediate expression (but was inducible late). All three promoters are useful, although Kan is preferred.

Previous work demonstrated the feasibility of using live bacterial vectors for immunization against malaria. Immunization of mice with *Salmonella* expressing CSP and MSP-1 protected against *P. berghei*, and induced immune responses against *P. falciparum* MSP-1 [Sadoff, Science 240:336-8, 1988; Toebe, Am J Trop Med Hyg. 56:192-9, 1997; Wu, J Biotechnol. 83:125-35, 2000]. The anti-MSP-1 immune response did not require secretion of antigen from the bacterium or surface display. These data suggest that use of *Brucella* as a platform to deliver *P. berghei* antigens in vivo is highly likely to protect mice and other mammals against malaria. Vaccines that work in the *P. berghei* mouse model can be reconstructed with *P. falciparum* antigens. Safety and immunogenicity testing in mice and efficacy testing against blood stage infection in nonhuman primates can then lead to human trials.

Any promoter can be used for expression of the complementation DNA fragment or the heterologous antigen as long as it is recognizable by *Brucella*. It is preferred that the promoter promotes transcription of antigen genes when the *Brucella* host is inside mammalian cells. To that end, it is preferred that the promoter be a *Brucella* promoter. One problem that we overcame was the technical issue of the choice of transcriptional control in expressing foreign antigens in *Brucella* is, since *Brucella* promoters generally are not well characterized. We determined that fusions of a heterologous gene to the purE upstream region appears to give low level constitutive expression under the conditions we've examined. The groES promoter gives intermediate expression inducible in stationary phase. The fusion of the heterologous aphA promoter in the Roop group's pBBR1MCS-6Y plasmid gives high constitutive expression in *Brucella*. The virB promoter is also contemplated, because of its intracellular transcriptional induction.

This invention may be used in the simultaneous vaccination of individuals against multiple diseases, so it is of potential benefit to any government agency providing medical care. Since *Brucella* is a potential biowarfare agent and thus a threat to U.S. military personnel, the Department of Defense would be a potential user of this technology. Live attenuated *Brucella* vaccines expressing antigens from other biothreat agents may provide broad protection against an array of bioweapons including engineered *Brucella*, and conceivably against infection from endemic disease during deployment. The Department of Homeland Security may also be interested in these vaccines against multiple bioterror threats, which maybe useful against potential bioterrorism aimed at agriculture and populace, e.g., *Brucella* and anthrax. Since *Brucella* causes disease in a variety of livestock, the U.S. Department of Agriculture would also have potential uses for this technology, since it offers the potential of single vaccination versus multiple animal diseases.

Furthermore, pharmaceutical and agribusiness firms would be interested in using this method for multivalent vaccines with intracellular delivery to create commercial multi-agent vaccines for people and livestock.

EXAMPLES

The invention in various embodiments and stages is further described in the following non-limiting examples.

Example 1

One experiment that indicated this approach was feasible was trans wboA complementation of the single mutant WRR51 within human macrophages.

Figure 1:
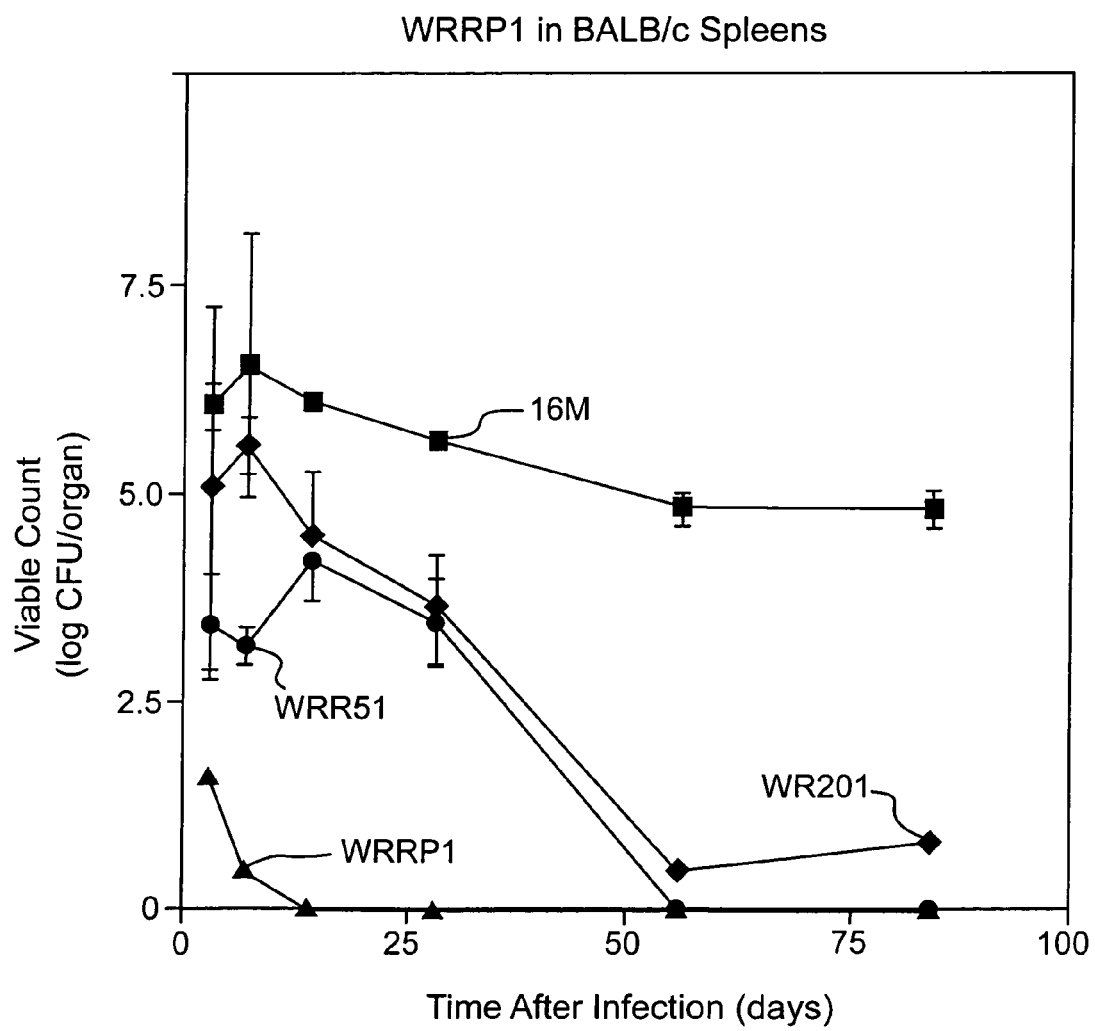
FIG. 1 shows attenuated strain WRRP1, having a wboA purEK dual deletion mutant of *Brucella melitensis* strain 16M known. Here WRRP1 persisted in BALB/c mouse spleens at low levels for only a week after IP infection, compared with purE and wboA single mutants, which infected in higher numbers and persisted for about 8 weeks.
Figure 2:
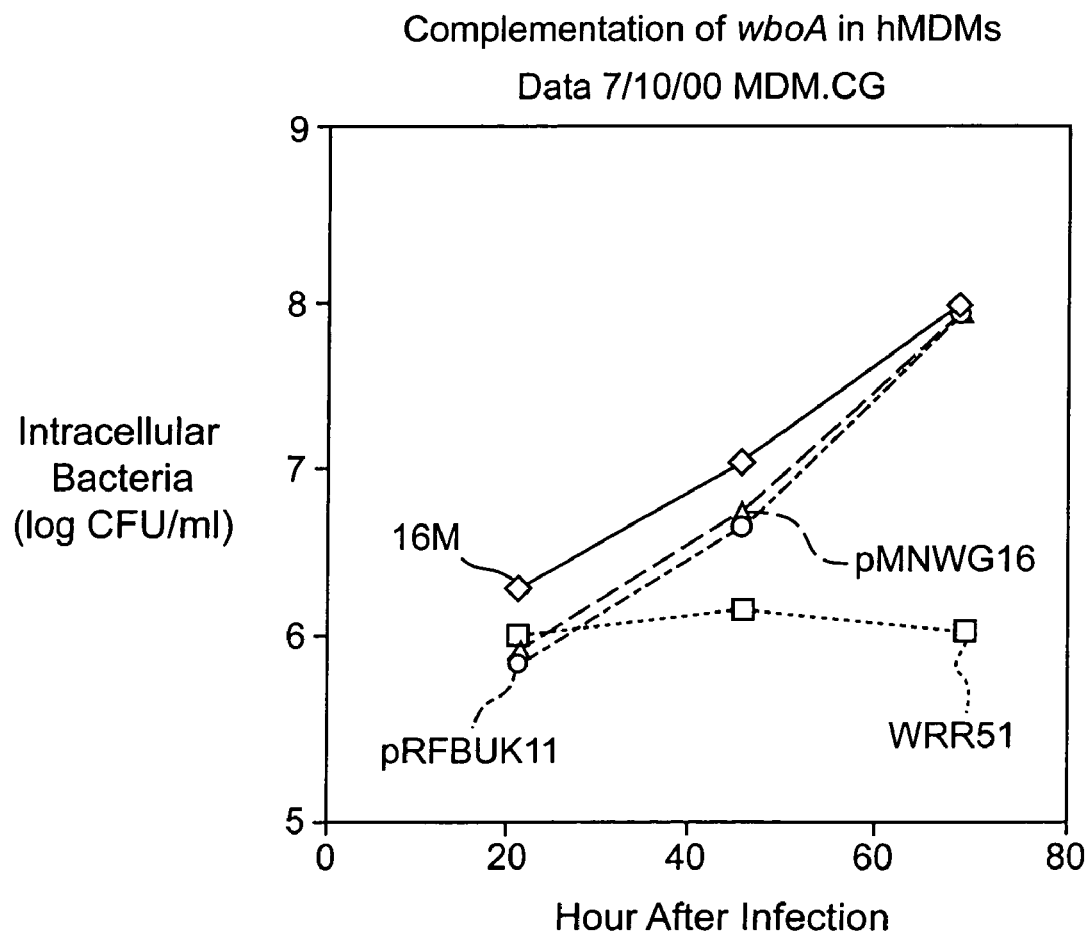
FIG. 2 shows trans wboA complementation of the single mutant WRR51 within human macrophages. The single mutant did not replicate in these cells over the 72 h timecourse of the experiment (diamonds), but the mutant complemented with a copy of wboA on a pBBR1-based plasmid (circles) replicated like wild type (squares). Also, green fluorescent protein (GFP) could be expressed on complementing plasmid pMNWG16 without hampering this replication (triangles), and all colonies recovered were green.

We expressed a heterologous antigen, Green Fluorescent Protein (GFP), on the complementing plasmid in WRR51. To determine if this plasmid complementation and expression of GFP would continue in the wboA mutant inside a host cell, we infected human monocyte-derived macrophages (hMDMs) with WRR51 containing pMNWG16, the complementing and GFP-expressing plasmid, on 10 Jul. 2000. We also infected these cells with WRR51 containing pRFBUK11, the non-GFP complementing plasmid, so we could make a comparison of these strains. Over the course of 72 hours inside these human macrophages, the survival and growth of both of these plasmid-complemented wboA *B. melitensis* mutant strains was near identical and was also very similar to that of the wild type parent of WRR51, strain 16M. Visual screens of bacteria recovered from hMDMs determined that WRR51 containing pMNWG16 clearly expressed GFP. See FIG. 2. The single mutant did not replicate in these cells over the 72 hour timecourse of the experiment (diamonds), but the mutant complemented with a copy of wboA on a pBBR1-based plasmid (circles) replicated like wild type (squares). Also, green fluorescent protein (GFP) could be expressed on complementing plasmid pMNWG16 without hampering this replication (triangles), and all colonies recovered were green.

The addition of the heterologous GFP gene to the wboA-complementing plasmid did not cause any diminution of survival within the human cell type that typically hosts *Brucella*. These tests demonstrated that we could express a heterologous antigen from a rough-complementing plasmid in a rough *Brucella* mutant containing a single defined nonreverting attenuating mutation without negatively affecting the intracellular survival and multiplication of the bacterium.

Example 2

We tested the simultaneous expression of a heterologous antigen and rough complementation from a plasmid in a *Brucella* strain containing additional attenuating mutation(s). Our goal was to use rough complementation for maintenance of the plasmid expressing the heterologous antigen, but also to have the resulting strain be attenuated for virulence, and thus a potential vaccine candidate.

Figure 3:
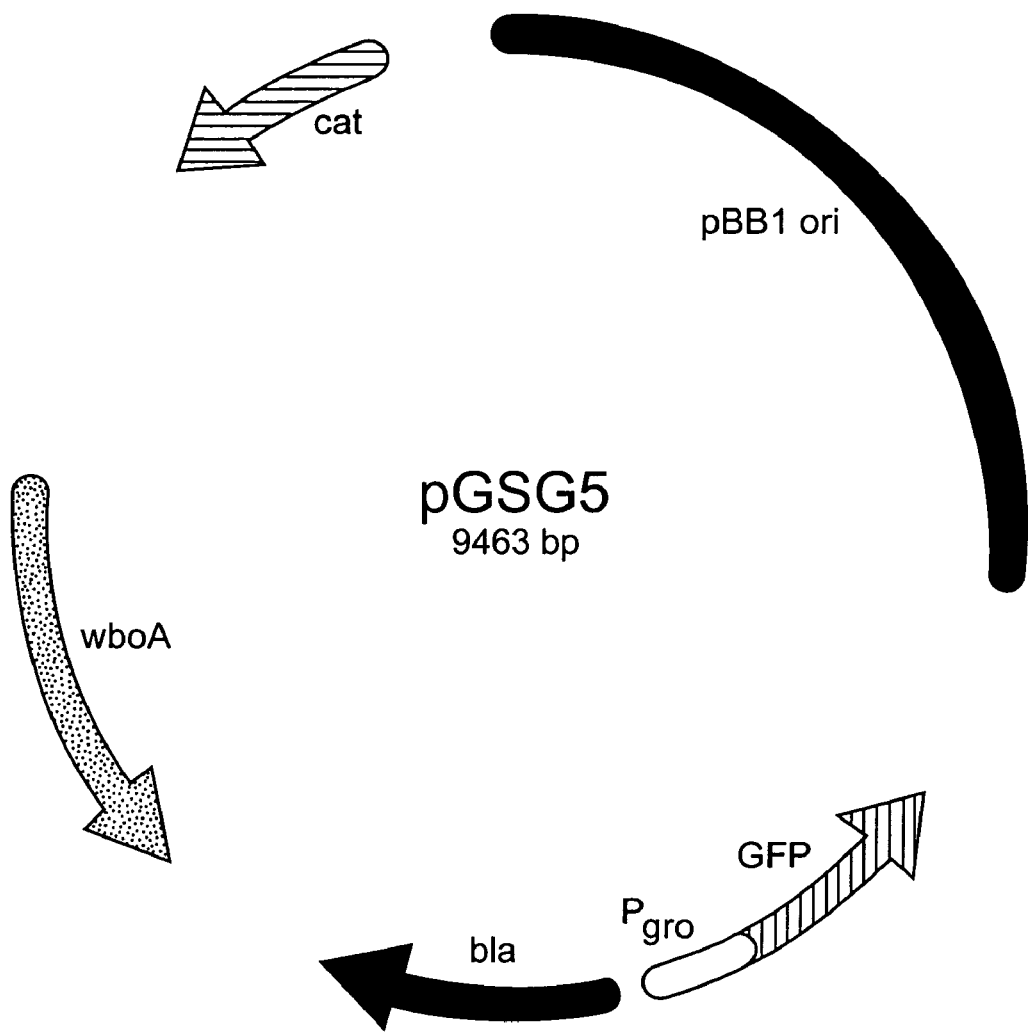
FIG. 3 shows plasmid pGSG5, containing GFP under the control of the groE promoter, an intact copy of wboA, and ampicillin resistance for in vitro selection in WRRP1, which already carries kanamycin and chloramphenicol markers.

We worked to find *Brucella* promoters that would provide a variety of levels of intracellular expression of heterologous antigens as we also began to work with different candidate antigens of clinical interest, including tetanus toxoid and malarial antigens. We combined all the elements in a plasmid we needed to test our concept: a heterologous antigen, GFP, fused to a *Brucella* promoter that gives significant intracellular expression, wboA to complement the rough defect in the host strain, and the correct antibiotic resistance marker to allow for selection of the plasmid in our test carrier strain, WRRP 1 which is Am$^r$ Kn$^r$. As noted above, WRRP1 is a dual deletion mutant of *B. melitensis* 16M with mutations in wboA and in purEK which we have demonstrated to be severely attenuated for virulence in a BALB/c mouse model. The plasmid was named pGSG5. (See FIGS. 3 and 10) Groups of BALB/c mice were infected with strain WRRP1 containing pGSG5 (WRRP1/pGSG5) and uncomplemented WRRP1 on 12 Nov. 2002. Five mice from each group were sacrificed at one week and at two weeks after infection and viable bacteria in the spleens of these mice were recovered. After one week, significantly higher numbers of WRRP1/pGSG5 were recovered than from uncomplemented WRRP1, which was present in very low numbers in the spleen of one of the five mice in the group. Additionally, the vast majority of the bacteria recovered from the spleens of the WRRP1/pGSG5-infected mice fluoresced under long-wavelength UV, indicating these bacteria were still expressing GFP. Less than 1% of the recovered WRRP1/pGSG5 bacteria lost GFP expression; these are likely to have lost the pGSG5 plasmid, since these colonies also lost the smooth phenotype provided by the wboA complementation. At two weeks after infection, none of the WRRP1-infected mice had bacteria in their spleens, while three of five WRRP1/pGSG5-infected mice were still infected. The percentage of the recovered WRRP1/pGSG5 had lost GFP expression and wboA complementation remained low at two weeks (a single colony-forming unit out of 70 recovered from the spleen of one of the five mice in the group). This selective pressure for in vivo maintenance of plasmid-borne heterologous antigen expression via rough mutation complementation is the basis of our multivalent vaccine delivery concept and is what makes it both innovative and promising.

Example 3

Figure 4:
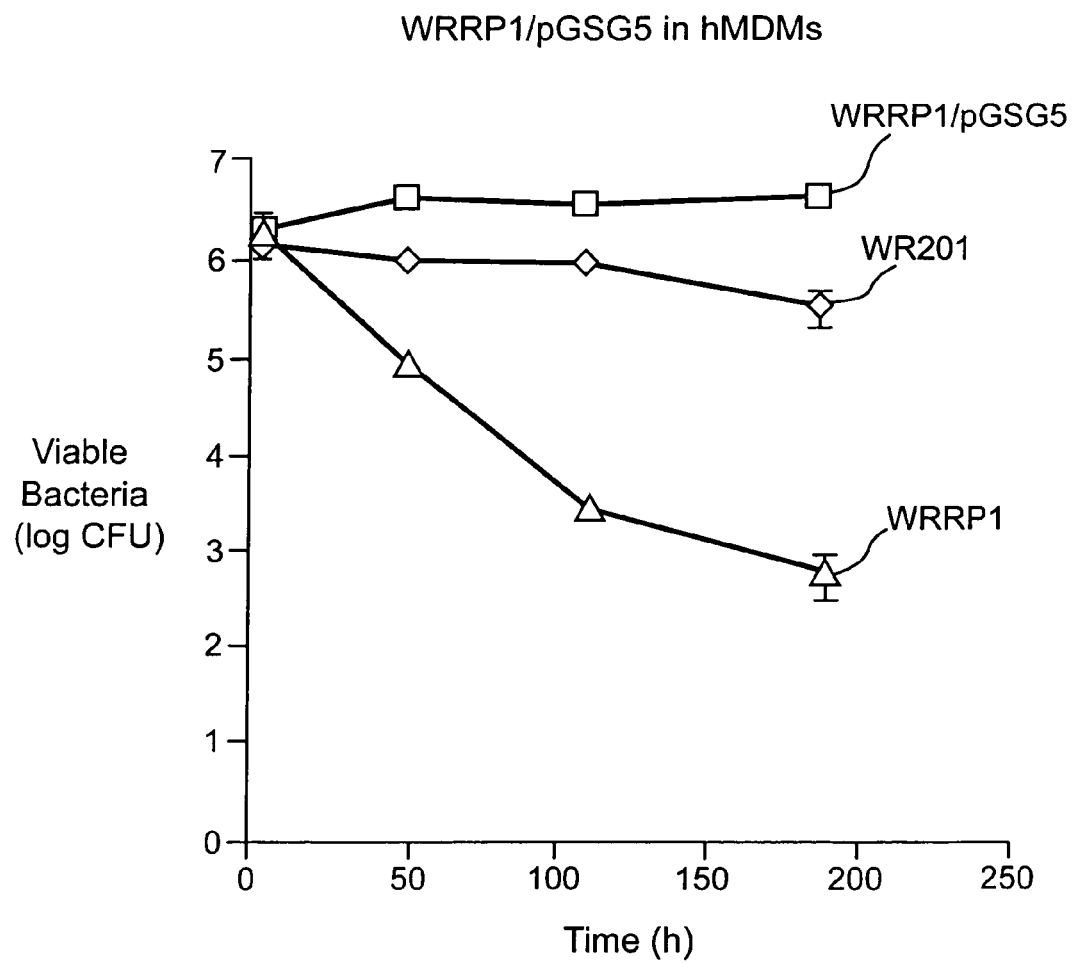
FIG. 4 shows the survival of WRRP1 carrying pGSG5 (squares) inside human macrophages over 200 hours.

We constructed a plasmid, pGSG5, containing GFP under the control of the groE promoter, an intact copy of wboA, and ampicillin resistance for in vitro selection in WRRP1, which already carries kanamycin and chloramphenicol markers. See FIGS. 3 and 10. As shown the by data represented in FIG. 4, inside human macrophages over 200 hours the survival of WRRP1 carrying pGSG5 (squares) was not significantly different from the survival of purine auxotroph WR201 (diamonds), whereas the uncomplemented WRRP1 decreased by three logs (triangles).

Figure 5:
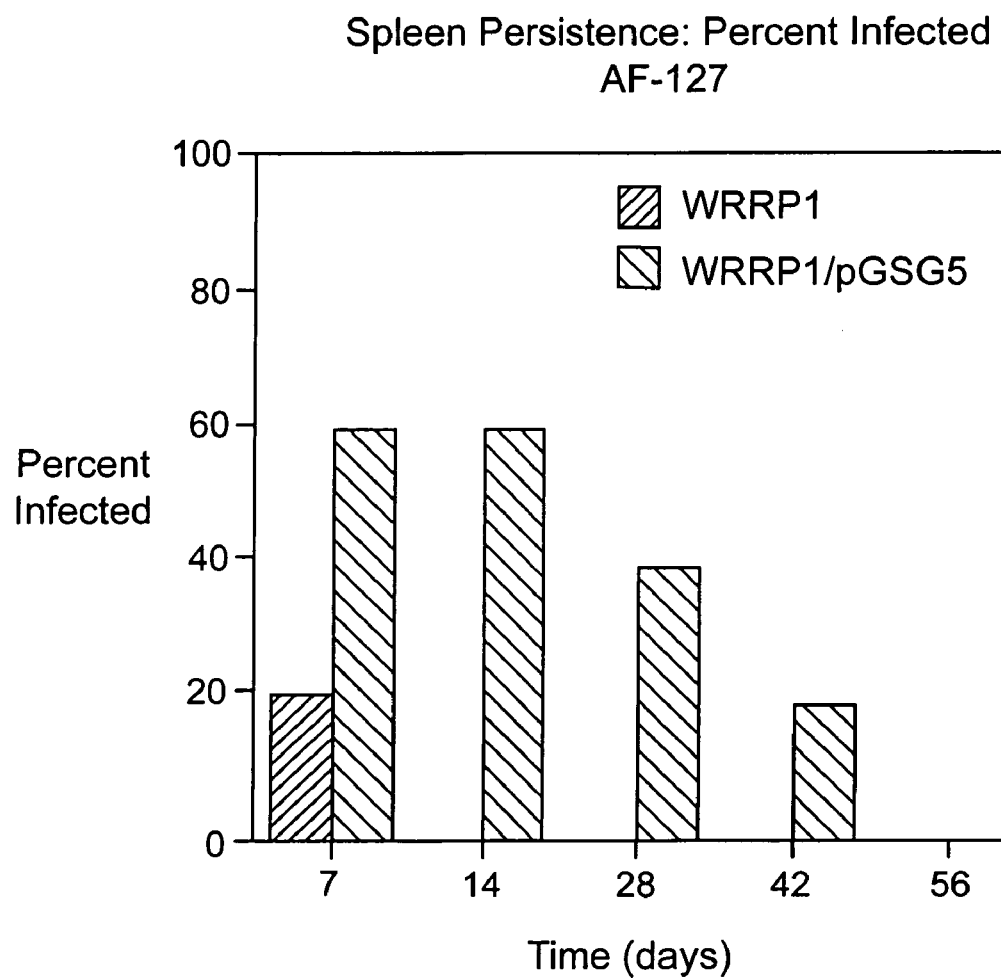
FIG. 5 shows spleen persistence, and percent infection in mice of uncomplemented WRRP1. The WRRP1 persisted in the spleen of one of five mice at one week only (light shading), while the strain carrying pGSG5 (dark shading) persisted in three of five mice at one and two weeks, in two of five at four weeks, one of five at six weeks, and then was cleared by eight weeks.

As shown by the data represented in FIG. 5, after introduction into some aging male BALB/c mice by the oral route, uncomplemented WRRP1 persisted in the spleen of one of five mice at one week only (light shading), while the strain carrying pGSG5 (dark shading) persisted in three of five mice at one and two weeks, in two of five at four weeks, one of five at six weeks, and then was cleared by eight weeks. The duration of persistence in the spleen was similar to that of the purine auxotroph WR201, however the numbers of viable bacteria recovered were consistently significantly lower than what we would have expected for a straight purE phenotype.

Figure 6:
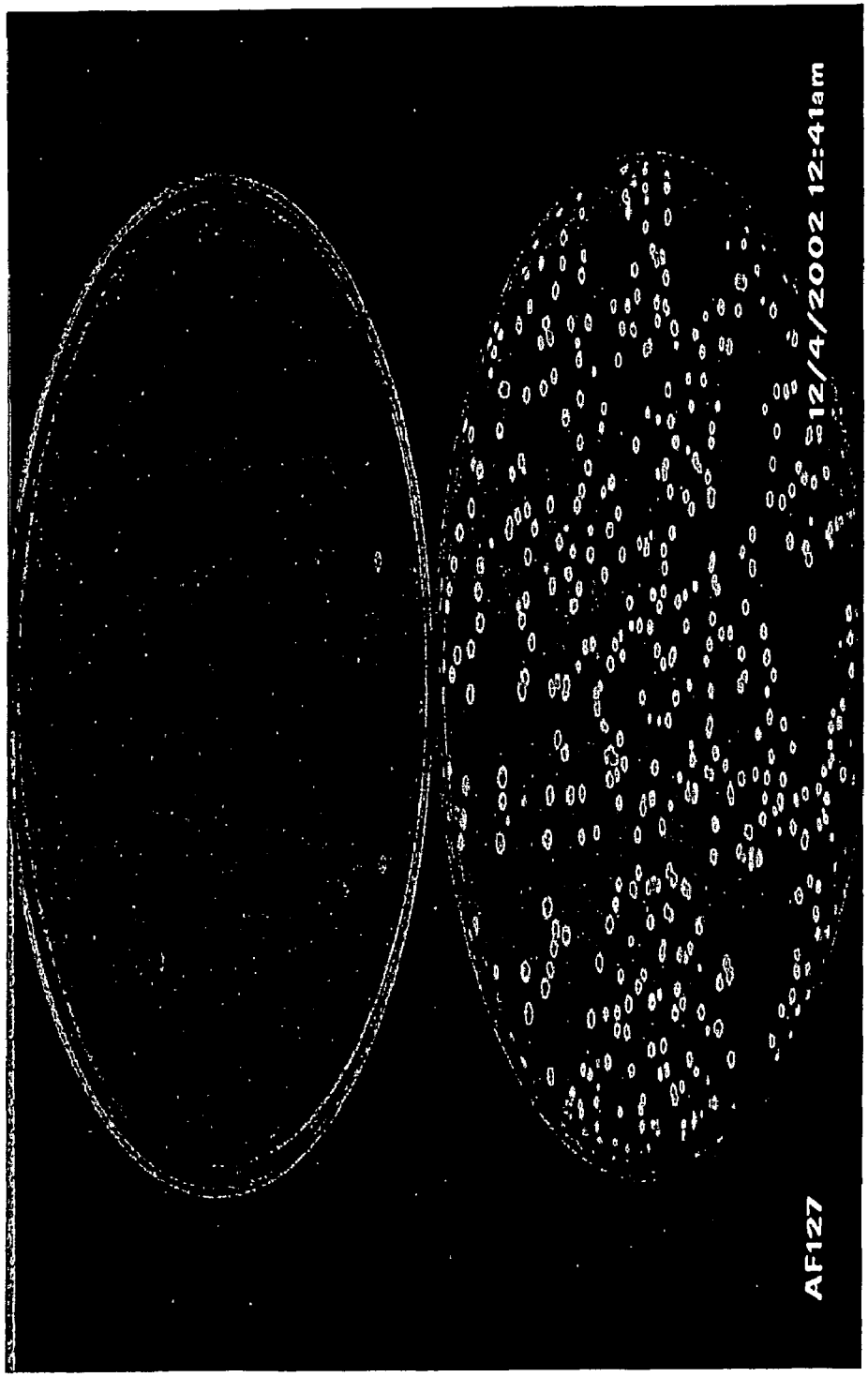
FIG. 6 shows two agar plates from experiment described in FIG. 5, visualized under UV (365 nm). On the left is the spleen neat plate containing the only colony forming units (CFUS) of WRRP1 recovered at one week after infection. On the right is a spleen neat plate from the plasmid complemented group at one week.

FIG. 6 shows two plates from that experiment visualized under UV (365 nm). On the left is the spleen neat plate containing the only colony forming units (CFUs) of WRRP1 recovered at one week after infection. On the right is a spleen neat plate from the plasmid complemented group at one week. One can see that these bacteria are fluorescent because they are expressing GFP. However, a small subpopulation of nongreen colonies can also be seen; these colonies were also rough, so they appear to have lost the plasmid. This was consistently seen in this group, but the nongreen population did not exceed 2% at any timepoint.

Figure 7:
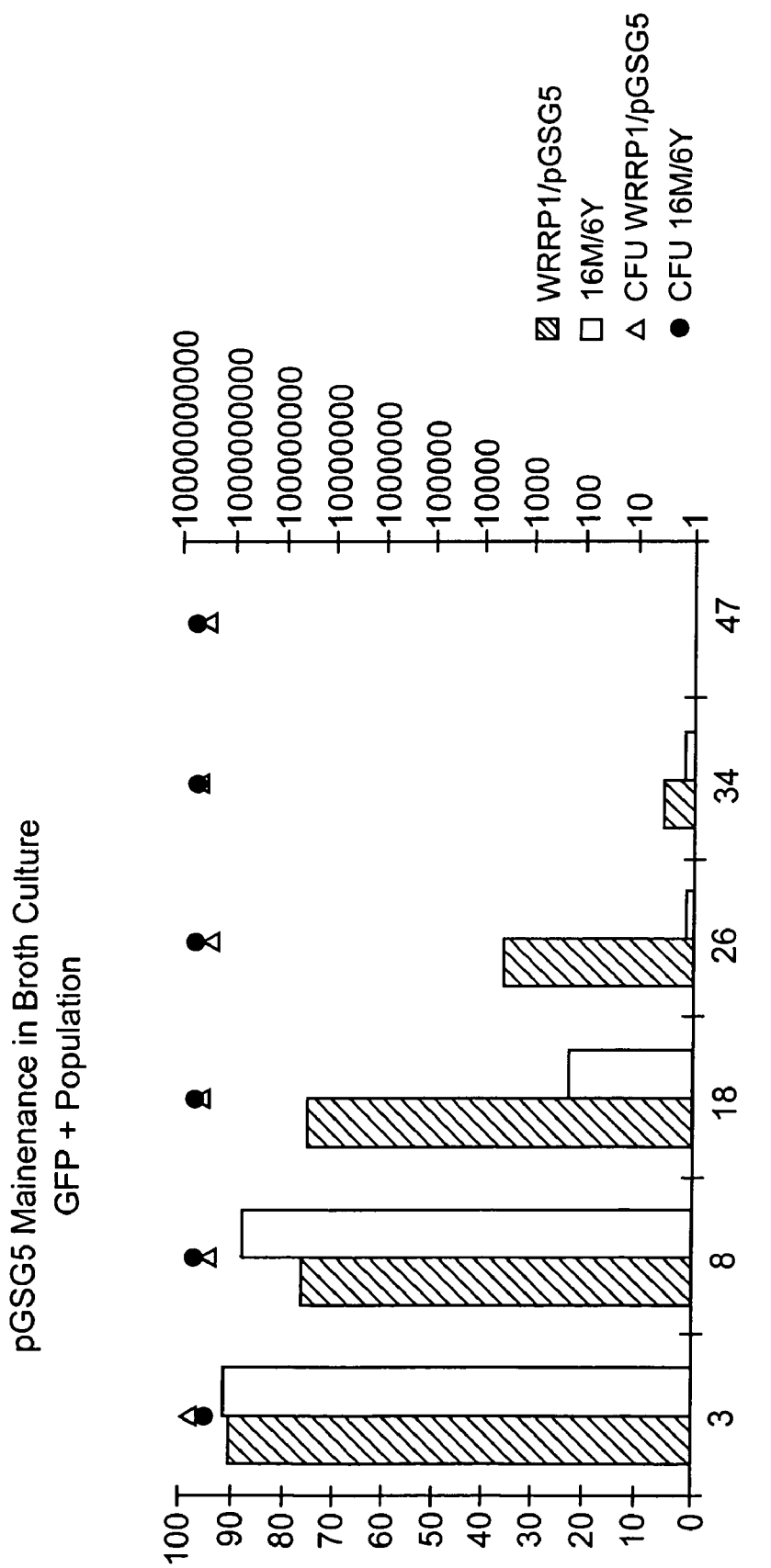
FIG. 7 tests whether loss of pGSG5 from WRRP1 was a real and reproducible attribute. Shown are the results of a multipassage culture in rich medium (*Brucella* Broth). Here we track the percentage of green CFUs recovered from a culture WRRP1 carrying pGSG5 compared with a culture of 16M bearing pBBR1MCS-6Y treated identically. A passage into fresh broth was made after each measurement. (The circles and triangles merely show that total CFU levels were comparable at all timepoints.) What is seen is that pGSG5 is in fact lost from WRRP1 under these conditions by 47 days. Interestingly, pBBR1MCS-6Y was lost from 16M more rapidly, indicating that the trans wboA complementation of WRRP1 may provide some selection for retention of the plasmid even in vitro. So this indicated to us that natural loss of plasmid is occurring in the mouse and may account for reduced spleen loads seen in complemented WRRP1 versus WR201.

To see if this loss of pGSG5 from WRRP1 was a real and reproducible attribute, we examined it in multipassage culture in rich medium (*Brucella* Broth). As shown in FIG. 7, we tracked the percentage of green CFUs recovered from a culture WRRP1 carrying pGSG5 compared with a culture of 16M bearing pBBR1MCS-6Y treated identically. A passage into fresh broth was made after each measurement. (The circles and triangles merely show that total CFU levels were comparable at all timepoints.) What is evident is that pGSG5 is in fact lost from WRRP1 under these conditions by 47 days. Interestingly, pBBR1MCS-6Y was lost from 16M more rapidly, indicating that the trans wboA complementation of WRRP1 may provide some selection for retention of the plasmid even in vitro. This indicated that natural loss of plasmid is occurring in the mouse and may account for reduced spleen loads seen in complemented WRRP1 versus WR201.

Example 4

We postulated that our invention would provide a novel platform for expression of malaria antigens in humans that may greatly enhance immunogenicity of malaria antigens and extend the utility of a live, attenuated human brucellosis vaccine. To test this, we constructed plasmids for the expression of *P. berghei* CSP and MSP-1 in *Brucella*. One goal was to find and clone *Brucella* promoters that would offer the range of in vivo expression levels needed to optimize Brucellar expression of different recombinant malarial antigens inside host macrophages. We used fluorescent reporter proteins as test heterologous antigens in this promoter search, which yielded three promoters with distinct levels of expression in *Brucella*. Since genes expressed in *Escherichia coli* are usually expressed in *Brucella* if necessary signals for transcription are present, and since these recombinant malaria antigens were expressed in *E. coli*, we could begin the studies of protective efficacy in mice.

Our accomplishments included:

- Development of a Polymerase Chain Reaction (PCR) method to fuse *Brucella* promoters with heterologous genes. This allows interchangeable combination of promoters and genes for rapid expression of heterologous antigens.
- Use of PCR to fuse the *Brucella* purE promoter to Enhanced Green Fluorescent Protein (EGFP) gene, DsRed red fluorescent protein gene, and the GFP gene. Flow cytometry confirmed GFP expressed at low constitutive level in *Brucella* from this promoter. EGFP and DsRed were not expressed from this promoter.
- Fusion of *P. berghei* MSP-1 and CSP to purE promoter by PCR and then moved into *Brucella*.
- On a plasmid in a rough *Brucella* mutant, we expressed both GFP under the control of kanamycin resistance (kan) promoter and a gene complementing the rough mutation. Complementation and GFP expression inside human macrophages demonstrated maintenance of an expression plasmid in an intracellular *Brucella* vaccine carrier.

Fusion of *P. berghei* MSP-1 to kan promoter by PCR and then moved it into *Brucella*.

Fusion of GFP to *Brucella* groES promoter by PCR and then moved it into *Brucella*. This construct expressed high levels of GFP in a purEK mutant *B. melitensis* vaccine candidate and is inducible in host macrophages.

Fusion of recombinant *P. berghei* genes encoding MSP-1 and CSP to groES promoter by PCR and then moved it into *Brucella*. We have CSP and MSP1 DNA under the control of the groE promoter.

Example 5

We devised and refined a PCR method for the fusion of *Brucella* promoters with genes for heterologous antigens. This approach allows for the mixing and matching of promoters and genes to rapidly optimize the expression of heterologous antigens, specifically *P. berghei* and *P. falciparum* proteins, in *Brucella* vaccine carriers.

We constructed fusion plasmids for the expression of heterologous fluorescent reporter proteins EGFP, DsRed and GFP under control of the *Brucella* purE promoter and moved plasmids into *B. melitensis*. Only GFP was expressed at low level, and this was not inducible in macrophages. We constructed plasmids to express recombinant *P. berghei* antigens MSP-1 and CSP behind the purE promoter and moved into *Brucella*.

In a *B. melitensis* rough mutant we expressed GFP at intermediate levels behind the kan promoter on a plasmid carrying a gene complementing the rough defect of the host strain. Rough complementation on the expression plasmid served to maintain it in the bacterium inside human macrophages, since rough strains are attenuated relative to smooth in mammalian hosts. This approach will insure the maintenance of expression plasmids in live *Brucella* vaccine carriers within host cells. We fused recombinant *P. berghei* MSP-1 to the kan promoter.

We fused GFP to the *Brucella* groES promoter. This construct yielded high levels of GFP expression in a *B. melitensis* purEK vaccine strain inducible in vivo. We fused recombinant *P. berghei* MSP-1 and CSP genes to the groES promoter. We have CSP and MSP1 DNA under the control of the groE promoter.

Example 6

Figure 8:
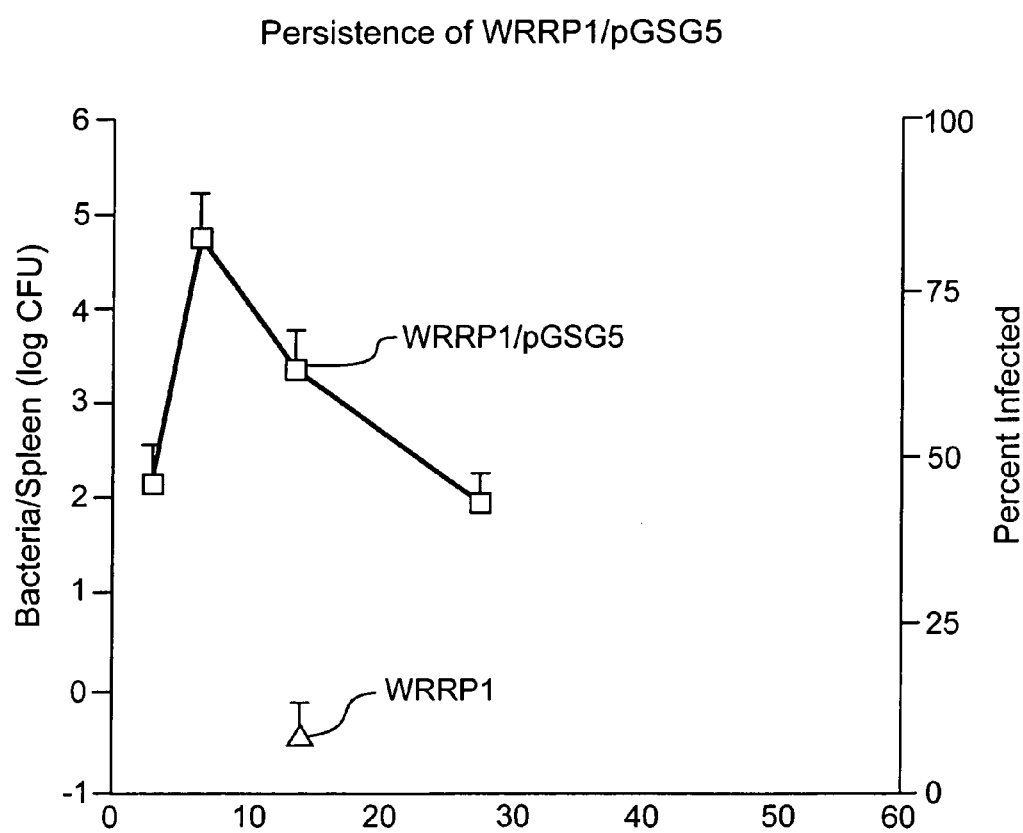
FIG. 8 shows the results of a repeat of the previous persistence experiment but with younger mice. Similar results were achieved. WRRP1 bearing pGSG5 again persisted for a much longer time and at vastly higher numbers than the uncomplemeted strain, and again was cleared from BALB/c spleens by 8 weeks. The data were more robust here, with lower variation; we saw 100% infection in the complemeted group through 2 weeks. Mean spleen loads were consistently higher and more comparable of what is characteristic for WR201, at least in the early timepoints. We also saw a single colony in the uncomplemented group at 2 weeks, interesting because we had never seen persistence beyond a week in any previous experiment (oral or intraperitoneal).

A repeat of the previous persistence experiment but with younger mice yielded similar results. See FIG. 8. WRRP1 bearing pGSG5 again persisted for a much longer time and at vastly higher numbers than the uncomplemeted strain, and again was cleared from BALB/c spleens by 8 weeks. The data were more robust here, with lower variation; we saw 100% infection in the complemeted group through 2 weeks. Mean spleen loads were consistently higher and more comparable of what is characteristic for WR201, at least in the early timepoints. We also saw a single colony in the uncomplemented group at 2 weeks, interesting because we had never seen persistence beyond a week in any previous experiment.

Looking at the dissemination of the complemented strain to the organs in these mice, as shown in FIG. 9, the numbers recovered from spleens exceeded the other organs, with the exception of the lungs at 3 days. Lungs and livers were also clear by eight weeks. There was low-level dissemination to inguinal lymph nodes up to two weeks. And here was a low level and transient dissemination to the male reproductive organs, gone after 1 week. Early clearance from the male reproductive organs is an aspect that distinguishes WRRP1 bearing pGSG5 from the purine auxotroph WR201, whose persistence in these organs was extended in both mice and nonhuman primates. This indicated increased attenuation is perhaps due to decay of smoothness by loss of the complementing plasmid in the host. This attenuation indicates that severely attenuated WRRP1 with its rough defect trans complemented in this way may be a safer alternative to WR201 and may be as effective in immunizing against *Brucella*. WR201 was our most effective vaccine to date, providing sterile immunity in nonhuman primates.

The Sequence Listing below includes the following sequences.

SEQ ID NO: 1 is a DNA sequence encoding the wboA (RfbU) gene, a mannosyltransferase.

SEQ ID NO: 2 is an amino acid sequence of the wboA (RfbU) protein.

The invention claimed is:

1. An immunogenic composition comprising a live *Brucella* host cell having a rough phenotype, which host cell contains at least two mutations so as to effect sufficient attenuation such that upon exposure to a mammal the host cell will not exhibit full virulence of non-attenuated *Brucella*, wherein the host cell is transformed with a recombinant DNA construct replicable in *Brucella*, which DNA construct comprises:

(i) a promoter recognizable by *Brucella*, and
   (ii) a complementation DNA fragment which encodes a peptide required for lipopolysaccharide O-sidechain synthesis so as to effect lipopolysaccharide O-sidechain synthesis in vivo and which is operably linked to the promoter and which complements a rough-conferring mutation in the host cell, thereby effecting a smooth phenotype in the host cell, wherein the association between the *Brucella* host cell and the DNA construct is such that following exposure to a mammal the DNA construct gradually separates from the *Brucella* host cell, whereupon the *Brucella* host cell reverts to a rough phenotype that is rapidly and safely cleared from the mammal.

2. The immunogenic composition of claim 1, wherein the *Brucella* host cell comprises a *Brucella* DNA fragment containing a stable non-reverting deletion mutation, having the nucleotide sequence of SEQ ID NO: 1 modified to delete nucleotides from position 1067 to position 1671.

3. The immunogenic composition of claim 1, wherein the *Brucella* host cell is *Brucella melitensis*.

4. The immunogenic composition of claim 1, wherein the *Brucella* host cell is WRRP1, having ATCC accession number PTA-3753.

5. The immunogenic composition of claim 4, wherein *Brucella* host cell WRRP1 has no antibiotic resistance markers.

6. The immunogenic composition of claim 1, wherein the promoter is a *Brucella* promoter.

7. The immunogenic composition of claim 1, wherein the complementation DNA fragment comprises the wboA gene.

8. An immunogenic composition comprising a live attenuated *Brucella* host cell having a rough phenotype, which host cell contains at least two mutations so as to effect sufficient attenuation such that upon exposure to a mammal the host cell will not exhibit full virulence of non-attenuated *Brucella*, wherein the host cell is transformed with a recombinant DNA construct replicable in *Brucella*, which DNA construct comprises:

(i) a DNA fragment operably linked to a first promoter recognizable by *Brucella*, and encoding a heterologous antigen; and
   (ii) a complementation DNA fragment which encodes a peptide required for lipopolysaccharide O-sidechain synthesis so as to effect lipopolysaccharide O-sidechain synthesis in vivo and which is operably linked to a second promoter recognizable by *Brucella*, and which complements a rough-conferring mutation in the host cell, thereby effecting a smooth phenotype in the host cell cell, wherein the association between the *Brucella* host cell and the DNA construct is such that following exposure to a mammal the DNA construct gradually separates from the *Brucella* host cell, whereupon the *Brucella* host cell reverts to a rough phenotype that is rapidly and safely cleared from the mammal.

9. The immunogenic composition of claim 8, wherein the *Brucella* host cell comprises a *Brucella* DNA fragment containing a stable non-reverting deletion mutation, having the nucleotide sequence of SEQ ID NO: 1 modified to delete nucleotides from position 1067 to position 1671.

10. The immunogenic composition of claim 8, wherein the *Brucella* host cell is *Brucella melitensis*.

11. The immunogenic composition of claim 8, wherein the *Brucella* host cell is WRRP1, having ATCC accession number PTA-3753.

12. The immunogenic composition of claim 8, wherein *Brucella* host cell WRRP1 has no antibiotic resistance markers.

13. The immunogenic composition of claim 8, wherein the promoter is a *Brucella* promoter.

14. The immunogenic composition of claim 8, wherein the heterologous antigen is selected from the group consisting of anthrax antigens, *Yersinia pestis* F1 and V antigens and F1-V fusion proteins, malaria circumsporozoite and merozoite antigens, *Plasmodium berghei* antigens, *Plasmodium falciparum* antigens, *Plasmodium vivax* antigens, *Plasmodium malariae* antigens, *Francisella* antigens, staphylococcal and streptococcal enterotoxin fragment antigens; *Burkholderia* antigens, *Coxiella* antigens, *Clostridium* epsilon toxoids, botulinum toxoids, smallpox antigens, mycobacterial antigens, cancer antigens, HIV antigens, tetanus toxoids, diphtheria toxoids, pertussis toxoid, *Helicobacter* antigens, *Borrelia* antigens, *Legionella* antigens, *Bartonella* antigens, vaccinia antigens, antigen-GFP fusions, tagged antigens 6his and V5, and fusions of antigens to secretory signals.

15. The immunogenic composition of claim 14, wherein the anthrax antigen is selected from the group consisting of *Bacillus anthracis* protective antigen and inactive variants of Edema Factor and Lethal Factor.

16. The immunogenic composition of claim 14, wherein the malaria antigens are CSP and MSP1 antigens of *Plasmodium berghei, Plasmodium falsiparum, Plasmodium vivax*, or *Plasmodium malariae*.

17. The immunogenic composition of claim 8, wherein the complementation DNA fragment comprises the wboA gene.

18. A vaccine against infection by brucellosis, comprising a live *Brucella* host cell having a rough phenotype, which host cell contains at least two mutations so as to effect sufficient attenuation such that upon exposure to a mammal the host cell will not exhibit full virulence of non-attenuated *Brucella*, wherein the host cell is transformed with a recombinant DNA construct replicable in *Brucella*, which DNA construct comprises:

(i) a promoter recognizable by *Brucella*, and
(ii) a complementation DNA fragment encodes a peptide required for lipopolysaccharide O-sidechain synthesis so as to effect lipopolysaccharide O-sidechain synthesis in vivo and which is operably linked to the promoter and which complements a rough-conferring mutation in the host cell, thereby effecting a smooth phenotype in the host cell, wherein the association between the *Brucella* host cell and the DNA construct is such that following exposure to a mammal the DNA construct gradually separates from the *Brucella* host cell, whereupon the *Brucella* host cell reverts to a rough phenotype that is rapidly and safely cleared from the mammal.

19. The vaccine of claim 18, wherein the *Brucella* host cell comprises a *Brucella* DNA fragment containing a stable non-reverting deletion mutation, having the nucleotide sequence of SEQ ID NO: 1 modified to delete nucleotides from position 1067 to position 1671.

20. The vaccine of claim 18, wherein the *Brucella* host cell is *Brucella melitensis*.

21. The vaccine of claim 18, wherein the *Brucella* host cell is WRRP1, having ATCC accession number PTA-3753.

22. The vaccine of claim 21, wherein *Brucella* host cell WRRP1 has no antibiotic resistance markers.

23. The vaccine of claim 18, wherein the promoter is a *Brucella* promoter.

24. The vaccine of claim 18, wherein the complementation DNA fragment comprises the wboA gene.

25. The vaccine of claim 18, wherein when the vaccine is administered to a vaccinee, the lipopolysaccharide O-sidechain polysaccharide is produced in vivo and an antibody to the lipopolysaccharide O-sidechain polysaccharide is produced by the vaccinee in response.

26. DNA construct pGSG5.

27. The immunogenic composition of claim 1, wherein the DNA construct would be cleared out from a mammal in about eight weeks or less.

28. The immunogenic composition of claim 1, wherein the *Brucella* host cell contains three mutations.

29. The immunogenic composition of claim 8, wherein the DNA construct would be cleared out from a mammal in about eight weeks or less.

30. The immunogenic composition of claim 8, wherein the *Brucella* host cell contains three mutations.

31. The vaccine of claim 18, wherein the DNA construct would be cleared out from a mammal in about eight weeks or less.

32. The vaccine of claim 18, wherein the *Brucella* host cell contains three mutations.

\* \* \* \* \*